US011029913B1

(12) United States Patent
Doyle, III et al.

(10) Patent No.: US 11,029,913 B1
(45) Date of Patent: *Jun. 8, 2021

(54) CUSTOMIZABLE REAL-TIME ELECTRONIC WHITEBOARD SYSTEM

(71) Applicant: C/HCA, Inc., Nahsville, TN (US)

(72) Inventors: Vincent Doyle, III, Mount Pleasant, SC (US); Robert Barnett Rhodes, Tallahassee, FL (US); Gina Marie Ragans, Tallahassee, FL (US); Sameer Sunilkumar David, Tallahassee, FL (US); Marne Lynn Owens, Tallahassee, FL (US); David Charles Sanderson, Tallahassee, FL (US); Janet McCallister, Tallahassee, FL (US); Lisa Ann Pitts, Tallahassee, FL (US)

(73) Assignee: C/HCA, Inc., Nashville, TN (US)

( * ) Notice: Subject to any disclaimer, the term of this patent is extended or adjusted under 35 U.S.C. 154(b) by 441 days.

This patent is subject to a terminal disclaimer.

(21) Appl. No.: 15/627,125

(22) Filed: Jun. 19, 2017

Related U.S. Application Data

(63) Continuation of application No. 15/299,617, filed on Oct. 21, 2016, now Pat. No. 9,690,538, which is a continuation-in-part of application No. 14/990,076, filed on Jan. 7, 2016, now abandoned.

(60) Provisional application No. 62/111,578, filed on Feb. 3, 2015.

(51) Int. Cl.
G06F 3/048 (2013.01)
G06F 3/14 (2006.01)
H04W 4/02 (2018.01)
G16H 80/00 (2018.01)
G16H 10/60 (2018.01)

(52) U.S. Cl.
CPC .......... G06F 3/1454 (2013.01); G16H 10/60 (2018.01); G16H 80/00 (2018.01); H04W 4/023 (2013.01)

(58) Field of Classification Search
None
See application file for complete search history.

(56) References Cited

U.S. PATENT DOCUMENTS 9,507,755 B1 * 11/2016 Kerzner .............. G06F 16/9535
2008/0248781 A1 10/2008 Perpinya et al.
(Continued)

OTHER PUBLICATIONS

U.S. Appl. No. 15/299,617, filed Oct. 21, 2016, Notice of Allowance dated Feb. 24, 2017 all pages.

Primary Examiner — Thanh T Vu
(74) Attorney, Agent, or Firm — Kilpatrick Townsend & Stockton, LLP

(57) ABSTRACT

Described herein is a system in which multiple display devices may be located remotely throughout a facility. The system receives location information for a number of users within the facility. The system is able to identify a set of users collocated with a particular display device and generate a set of configuration settings specific to that set of users. Information provided by the system, either in response to an information request or automatically, may be formatted and/or filtered according to the generated set of configuration settings. In some embodiments, the set of configuration settings may be compiled from each of the users in the set of users based on priority.

19 Claims, 20 Drawing Sheets

(56) References Cited

U.S. PATENT DOCUMENTS

| | | | |
|---|---|---|---|
| 2009/0125332 A1* | 5/2009 | Martin | G06Q 10/00 705/3 |
| 2010/0082371 A1* | 4/2010 | Kamp | G16H 10/60 705/3 |
| 2013/0017780 A1* | 1/2013 | Rose | H04W 4/16 455/41.1 |
| 2013/0204637 A1* | 8/2013 | Vanderveen | G06Q 10/00 705/2 |
| 2014/0279948 A1* | 9/2014 | Mahate | G06F 16/24578 707/692 |
| 2015/0026708 A1 | 1/2015 | Ahmed et al. | |
| 2015/0279335 A1 | 10/2015 | Ripp et al. | |
| 2016/0065629 A1 | 3/2016 | Emoff et al. | |
| 2016/0139782 A1 | 5/2016 | Scott et al. | |
| 2016/0248926 A1 | 8/2016 | Yasuda | |
| 2016/0366468 A1 | 12/2016 | Seo | |

* cited by examiner

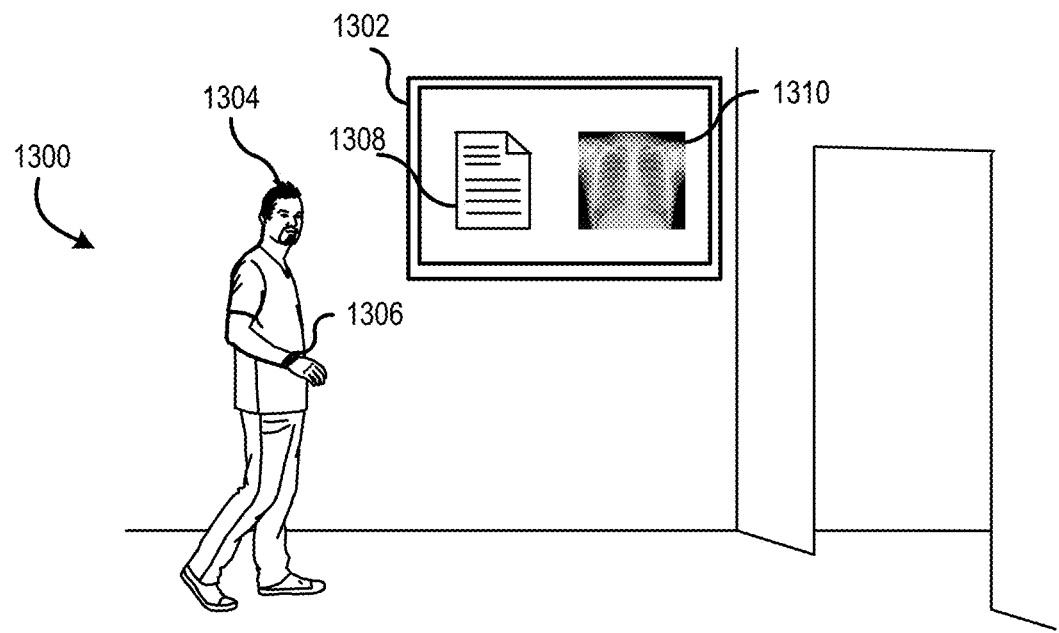
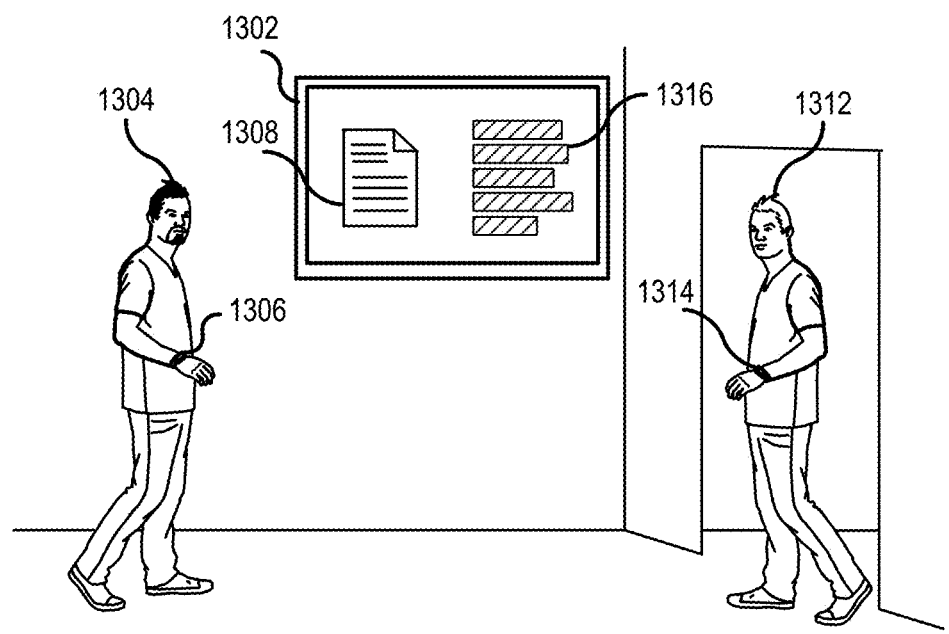
FIG. 13

SKYLINE FACILITY — 1902, 1910

| | | |
|---|---|---|
| USER GOALS<br>• Call Nurse for Assist<br>• Control Glucose<br>• Safety<br><u>1908</u> | NURSE — LAKESHA RN 6758<br>MYCARE — MINDY NT<br>ATTENDING — DR ARONS — <u>1904</u> | Name: DAV, SH<br>Room: 602 – A<br>Phone: 555-769-7602<br>PREFERRED LANGUAGE<br>English<br>DIET<br>Carb-Restricted Diabetic Diet |
| LAST PAIN MED<br>4/17/2016 11:32 AM | ACTIVITY — Bedrest | ANTICIPATED DISCHARGE |
| SCHEDULE<br>There are no procedures currently scheduled | PAIN LEVEL<br>Dr. Whitley, Phlebotomist has entered Room 602 — 1906 | GLUCOSE |

FIG. 19

CUSTOMIZABLE REAL-TIME ELECTRONIC WHITEBOARD SYSTEM

CROSS-REFERENCES TO RELATED APPLICATIONS

This application is a continuation of and claims the benefit of U.S. Non-Provisional application Ser. No. 15/299,617, filed Oct. 21, 2016, which is a continuation in part of and claims the benefit of U.S. Non-Provisional application Ser. No. 14/990,076, filed Jan. 7, 2016, which is a non-provisional of and claims the benefit of U.S. Provisional Application No. 62/111,578, filed Feb. 3, 2015. The entire disclosures of the above applications are hereby incorporated by reference, for all purposes, as if fully set forth herein.

BACKGROUND

In many industries, data related to a particular target user (i.e., user-specific data) may be spread across multiple databases or stored in separate data stores. This data is often stored in specialized data stores related to a number of different sources based on services and/or functions performed by those sources. Even if a target user could aggregate each of his or her records, differences in formats/variable usage often cause the data to be presented in a way that is not easily understood by a typical user. Accordingly, a customizable platform is needed to ensure that each time that a target user is presented with data, the target user is presented with the data that he or she would best understand.

Additionally, a number of presenters may be tasked with presenting data to a target user (e.g., presenters may be tasked with presenting data to a user). When the data to be presented is provided by multiple sources, it can often comprise a variety of incompatible formats. The presenter may need to search for the particular piece of data that he or she wishes to present. This can take up valuable time that would be best spent with the current target user or another target user. Accordingly, a customizable platform is needed to ensure that a presenter is able to present the data that he or she is interested in presenting as quickly and efficiently as possible.

BRIEF DESCRIPTION OF THE DRAWINGS

Various embodiments in accordance with the present disclosure will be described with reference to the drawings, in which:

FIG. 13 depicts an example of user presentation and restriction in accordance with at least one embodiment of the invention;

FIG. 19 illustrates an example of a graphical user interface display that may be implemented on an electronic display device in accordance with at least some embodiments.

DETAILED DESCRIPTION

Figure 1:
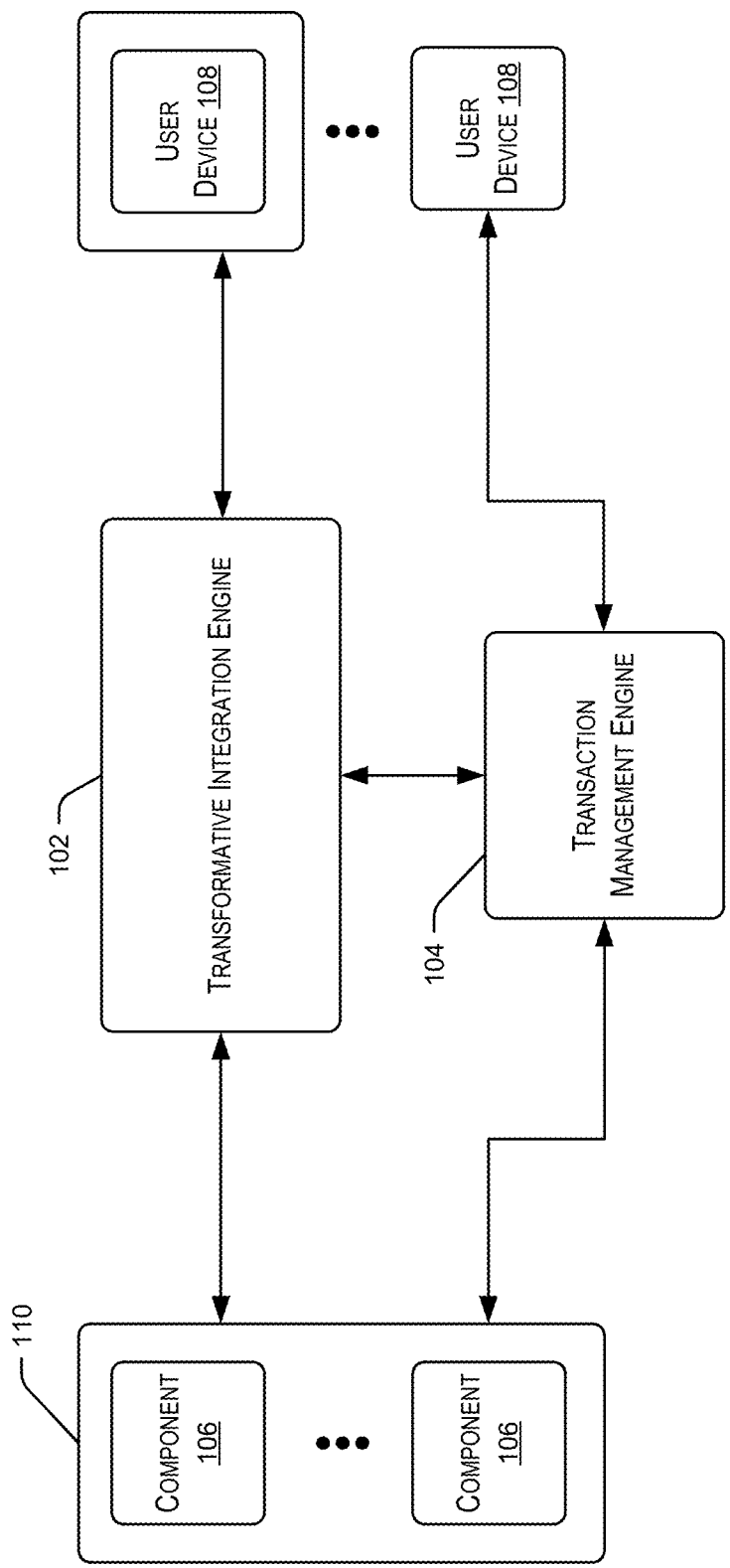
FIG. 1 is an example block diagram illustrating an environment in which techniques relating to executing reservation of resources for authorized users as described herein may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims. Furthermore, well-known features may be omitted or simplified in order not to obscure the embodiment being described.

Embodiments of the present disclosure are directed to, among other things, a system of customizable electronic display devices, input sensors (e.g., cameras, accelerometers, biometric sensors, etc.), real-time location system (RTLS) technology, and mobile devices that are used to track assets and provide real-time information to a user via any one of the customizable electronic display devices. In particular, the disclosure is directed to a system that enables customized presentation of timely medical information to a hospital user by a presenter. In accordance with at least one embodiment, requests to display information may be made via a mobile device. The mobile device may be part of the overall hospital system or it may be owned and operated by an individual via an installed application.

In accordance with at least one embodiment, user-related medical data is aggregated from a number of sources into a single database. An application layer may then be built upon the database in order to manage the user data. Data in the database may be updated periodically or dynamically and update queries may be made sequentially or in parallel. This data may then be filtered and presented to a user upon request, automatically (e.g., without human intervention and/or without receiving a request), or when certain conditions are met. The format or order that information is presented in may be fully customized. Additionally, the information may be presented in a particular format based on clinical or demographic requirements associated with a particular user. For example, information presented to a user that is associated with poor eyesight may be displayed in a larger font size.

In accordance with at least one embodiment, the disclosure may be directed to the setting and tracking of user goals. For example, a presenter may set goals for a particular user. In this example, the user is able to see his or her current objectives as well as any progress made toward their completion. Furthermore, tracking of goals may be automatic, or without the user direct interaction with the display device. For example, if a presenter would like a user to get some exercise; he or she may set a goal for the user to get up and walk around the building. A location tracking system could then be used to track the user's progress throughout the building and provide a progress bar or an indication that the goal has been met.

In accordance with at least one embodiment, the disclosure may be directed to presenting or preventing the presentation of information based on location indicators. For example, upon a presenter's entrance into a room containing a user, the display may present his or her name and specialty. If the user is being served food, information related to the meal (such as a menu or number of calories) might be presented. When a piece of medical equipment is present in the room, a description of the use and/or the specifications of the equipment may be displayed. In addition to determining what data to present based on who or what is in the room, data might also be prevented from being displayed based on who is in the room. For example, sensitive medical data may be removed from the display device when two users are present in a room without a presenter.

Referring first to FIG. 1, a block diagram of an embodiment of a medical provider network 100 is illustrated. The medical provider network 100 includes a plurality of elements connected with directional arrows. The directional arrows not only indicate that the elements are connected, but also indicate the direction that data may flow with respect to the various elements.

For example, data may flow between the following elements of the medical provider network 100: a transformative integration engine 102 and a transaction management engine 104.

Generally, the transformative integration engine 102 is configured to collect and aggregate medical-related data from components of the medical provider network 100 and components outside of the medical provider network 100. Once the transformative integration engine 102 collects and aggregates the medical-related data, it may perform one or more operations with respect to the data and store it in a data store. This stored medical-related data can then be accessed by components within and without the medical provider network 100.

The medical-related data is transmitted throughout the medical provider network 100 in accordance with any suitable transmission protocol. Generally, the transaction management engine 104 is configured to manage the flow of such transmissions within the medical provider network 100. Thus, the transaction management engine 104 receives indications of transmissions of medical-related content and tracks the origination locations of the transmissions, the destination locations of the transmissions, and any locations there between.

The medical provider network 100 includes one or more components 106 and one or more user devices 108. The one or more components 106 are configured to share medical-related data with the transformative integration engine 102, the transaction management engine 104, and each other via one or more communication networks. The one or more user devices 108 are configured to access medical-related data collected by the transformative integration engine 102 and provide their own medical-related data. Users of the one or more user devices 108 may use such medical-related data to help the users make medical decisions. While the one or more components 106 and the one or more user devices 108 are illustrated as communicating via the transformative integration engine 102 and/or the transaction management engine 104, this specification is not so limited. For example, each of the one or more components 106 may communicate with each of the one or more user devices 108 directly via other or the same communication networks. Each of the one or more components 106 of the medical provider network 100 is an example of a device, medical equipment, a lab system, a business terminal, a clinical terminal, or the like that can receive and/or provide medical-related data as further detailed herein. Each of the one or more user devices 108 is an example of a user device that can receive and/or provide medical-related data as further detailed herein. In some examples, at least some of the one or more user devices 108 may function similar to at least some of the one or more components 106 and vice-versa. In other words, each of the one or more user devices 108 and each of the one or more components 106 may both provide data and access data within the medical provider network 100.

In some examples, the one or more components 106 are each associated with one or more medical provider organizations within the same or different medical provider networks. For example, certain ones of the one or more components 106 may be associated with a first medical provider organization, while other ones of the one or more components 106 may be associated with a second medical provider organization. Additionally, each of the one or more components 106 may be associated with a medical care facility 110. The medical care facility 110 illustrates an example of one medical care facility. The medical provider network 100, however, may include many different types of medical care facilities (e.g., urgent care facilities, outuser facilities, hospitals, clinics, and medical record service facilities) including many different types of components. In some examples, the one or more components 106 are not associated with one of the medical care facilities 110, but instead are included as part of an information systems company that manages medical-related data such as electronic medical records.

The one or more components 106, irrespective of which medical provider organization each belongs to, may be capable of receiving, generating, processing and/or transmitting medical-related data. Examples of the one or more components 106 include, for example, a user device (e.g., computer, mobile device, smart phone, laptop, electronic badge, set-top box, thin client device, tablet, pager, and other similar user devices), clinical lab equipment (e.g., fluid processing device, chemistry analysis device, coagulation analysis device, DNA analysis device, genetic analysis device, urinalysis device, hematology analysis device, immunology analysis device, and other similar lab equipment), medical equipment (e.g., surgery tools, imaging machines, and other similar medical devices), business and/or administrative device that can receive input from (for example) a nurse, administrator, receptionist, secretary or assistant (e.g. server, computer, mobile device, smart phone, laptop, electronic badge, set-top box, thin client device and other similar business and/or administrative devices), and other similar devices capable of generating medical-related data. The one or more components 106 also includes entities that collect, aggregate, and store medical-related data. Some of these entities may be third-parties that make medical-related data available to the transformative integration engine 102.

The one or more components 106 provide medical-related data using one or more formats, some of which can be proprietary. For example, a magnetic resonance imaging (MRI) machine (e.g., one of the one or more components 106) manufactured by company A, located within a first medical care facility (e.g., the medical care facility 110), and belonging to a first medical provider organization, may save and transfer data in a first format. An MRI machine (e.g., one of the one or more components 106) manufactured by company B, located within the first medical care facility (e.g., the medical care facility 110), and belonging to the first medical care provider, may save and transfer data in a second format. In some examples, medical-related data from certain components is transformed, translated, or otherwise adjusted to be recognizable by the transformative integration engine 102. Thus, continuing with the example from above, when the MRI machines manufactured by companies A and B are located within the first medical care facility belonging to the first medical care provider, they may nevertheless save and transfer data in different formats. In some examples, the one or more components 106 communicate using the Health Level-7 (HL7) standard for hospital information systems or any other suitable format.

The transmission of medical-related data from the one or more components 106 to the transformative integration engine 102 may be triggered by a variety of different events. For example, the medical-related data may be transmitted periodically, upon detection of an event (e.g., completion of an analysis or end of a procedure), upon detection of an event defined by a rule (e.g., a user-defined rule), upon receiving user input triggering the transmission, or upon receiving a data request from the transformative integration engine 102. Each transmission can include, e.g., a single record pertaining to a single user, procedure, or analysis or multiple records pertaining to multiple users, procedures, or analyses.

In some examples, at least some of the one or more user devices 108 are associated with the medical care facility 110. At least some of the one or more user devices 108 may not be associated with the medical care facility 110 or any other medical care facility. Similar to the one or more components 106, the one or more user devices 108 may be capable of receiving, generating, processing and/or transmitting medical-related data. Examples of the one or more user devices 108 include, for example, a computer, a mobile device, a smart phone, a laptop, an electronic badge, a set-top box, a thin client device, a tablet, a pager, and other similar user devices). The one or more user devices 108 may differ from the one or more components 106 because the one or more user devices 108 may be configured to run one or more applications developed for interacting with the medical-related data collected by the transformative integration engine 102. For example, those user devices of the one or more user devices 108 that are not associated with the medical care facility 110 may be configured to run one or more third-party applications that may rely in part on the medical-related data gathered by the transformative integration engine 102.

Each of the one or more components 106 and the one or more user devices 108 may be utilized by one or more users (not shown). Each of the one or more users may be associated with one or more medical provider organizations. For example, one of the one or more users can be associated with a medical provider organization as a result of being employed by the organization, physically located at a location of the organization, being an agent of the organization or receiving a medical service from the organization.

The connections between the one or more components 106 and the one or more user devices 108 and the transformative integration engine 102 and the transaction management engine 104 are illustrated by a plurality of bi-directional arrows indicating that medical-related data may flow therebetween. The medical-related data flows in either direction within the medical provider network 100 (e.g., from the transformative integration engine 102 and the transaction management engine 104 towards the one or more components 106 and/or the one or more user devices 108 or to the transformative integration engine 102 and the transaction management engine 104 from the one or more components 106 and/or the one or more user devices 108). The connections between the one or more components 106 and the one or more user devices 108 and the transformative integration engine 102 and the transaction management engine 104 can include any suitable network connection. A connection can be configured to support communication over a wireless medium, e.g., using Wi-Fi (IEEE 802.11 family standards), Zigbee, Bluetooth® (a family of standards promulgated by Bluetooth SIG, Inc.), Bluetooth Low Energy or other protocols for wireless data communication. In some instances, a connection can include a wired connection.

In some examples, the one or more components 106 and the one or more user devices 108 may communicate with the transformative integration engine 102 and the transaction management engine 104 via different information formats, different proprietary protocols, different encryption techniques, different languages, different machine languages, and the like. As will be discussed with reference to FIG. 2, the transformative integration engine 102 is configured to receive these many different communications from the one or more components 106, and in some examples from the one or more user devices 108, in their native formats and transform them into any of one or more formats. The received and/or transformed communications can be transmitted to one or more other devices (e.g., the transaction management engine 104, an entity device and/or a user device) and/or locally or remotely stored. In some examples, the transformative integration engine 102 receives medical-related data in the HL7 format or conforming to any other suitable format and/or is configured to transform received data to conform with the HL7 format.

In some examples, the medical provider network 100 may not include the transformative integration engine 102, or may include part of the functionality described herein. For example, when the communications between the one or more user devices 108 and between the one or more components 106 are in the same format, the transformative integration engine 102 may not be required to transform the communications into other formats.

As used herein, medical-related data can include, for example, health information that is created or received by a presenter, a processed or unprocessed version of medical data detected by medical equipment, and/or user-identified data. Medical-related data can include information that identifies a user, such as personal information and/or demographic information. For example, the information can identify a user's name, age, sex, race, physical address, phone number, email address and/or social security number. Medical-related data may include information collected by a health plan, a public health authority, an employer, a life insurer, a school or university, or a health care clearinghouse that relates to the past, present, or future physical or mental health or condition of any individual.

Medical-related data can include financial and/or insurance information corresponding to the user. For example, the information can identify an insurance company, insurance plan, member identification number, group number, insurance contact information (e.g., address and/or phone number), deductible information, out-of-pocket information, copay information, an employer, an occupation and/or salary information.

Medical-related data can include medical-history information, such as past diagnoses, past or present symptoms or past procedures and/or corresponding dates (e.g., of diagnoses, symptom initiations and/or procedures). Medical-related data can identify past or present medications being taken by or having been prescribed to the user and corresponding dates. In some examples, the medical-related data can identify orders pharmacology orders, whether associated with a patient, doctor, or otherwise.

Medical-related data can include an identification of one or more medical services having been, being or having been requested by a user. A medical service can include, for example, an evaluation performed by a medical care professional, a medical test, a surgery and/or other procedure. Medical-related data can identify a medical test or analysis that was performed or prescribed and/or a result of the test or analysis. For example, information can indicate that a test (e.g., lab test, MRI, x-ray, CT scan, echocardiography, EKG, EEG, EMG, or ultrasound) was performed on a particular date and/or by a particular entity and can further include a processed and/or unprocessed result of the test (e.g., a count or level; an indication as to whether a test result is normal; and/or an indication as to whether a particular feature (e.g., a fracture, tumor, lesion, slowed nerve conduction) was observed and/or a magnitude of the feature). Medical-related data can include any information pertaining to genes of generic populations, users, sets of users, living organisms, and of any other suitable group. Information pertaining to genes includes, for example, genomic information (e.g., DNA sequencing), hereditary information, classical genetic information, molecular genetic information, any other suitable information pertaining to genes.

Medical-related data can identify one or more care providers or institutions. The care provider and/or institution can be one associated with recent or past care and/or with the user. For example, data can be transmitted for a user admitted in Hospital A and being treated by Specialist B, though the data can also identify that the user's primary care physician is Doctor C.

Medical-related data may, or may not, selectively pertain to a particular user. For example, non-user-specific data may include a price of a prescription, a recommended or approved dosing schedule for a medication, a work schedule for a physician, an acceptance criteria for a clinical study, non-user-specific data can include information pertaining to the operation of a medical care facility, financial information, administrative information, and generic clinical information.

Medical-related data can, depending on the implementation, include individually identifiable health information and/or de-identified information. Individually identifiable health information includes, for example, health information, including demographic information collected from an individual that is created or received by a presenter, health plan, employer, or health care clearinghouse; and that relates to the past, present, or future physical or mental health or condition of an individual, the provision of health care to an individual, or the past, present, or future payment for the provision of health care to an individual; and that identifies the individual; or, with respect to which there is a reasonable basis to believe, can be used to identify the individual. De-identified information includes information that cannot be used on its own or with other information to identify a person to whom the information belongs.

As used herein, medical-related data can include protected health information, which can include individually identifiable health information that is transmitted by electronic media, maintained in electronic media, or transmitted or maintained in any other form or medium. Examples of protected health information, include, for example any information about health status, provision of health care, or payment that can be linked to a particular user and may include any of the following information capable of identifying the user: names, geographic identifiers, dates directly relating to the user, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

The one or more components 106 of the medical care facility 110 can include and/or has access to a local or remote memory for storing generated medical-related data. In some examples, the medical-related data is stored by one or more servers local to the medical care facility 110. Such storage may enable the medical care facility 110 to retain locally medical-related data pertaining to its own users prior to (or in conjunction with) the medical-related data being shared with the transformative integration engine 102 and/or the transaction management engine 104. In some examples, the one or more servers of the medical care facility 110 share medical-related data directly with a record service (not shown), and the record service makes the medical-related data available to the transformative integration engine 102 and/or the transaction management engine 104. Once an electronic medical record is updated at the medical care facility 110, an indication of the update may be provide to the record service. The record service may then update a corresponding record associated with the electronic medical record.

The record service can be granted access to the medical-related data generated and/or transmitted by the one or more components 106. In some examples, the record service includes a server or a plurality of servers arranged in a cluster or the like. These server(s) of the record service can process and/or store medical-related data generated by the one or more components 106. For example, one or more records can be generated for each user (e.g., each record corresponding to a different entity or being shared across entities). Upon receiving a communication with medical-related data from an component (or medical care facility), the record service can identify a corresponding record and update the record to include the medical-related data (or processed version thereof). In some examples, the record service provides medical-related data to the transformative integration engine 102.

The medical care facility 110 is a facility at which care is provided to users. Irrespective of the type of medical care facility, the medical care facility 110 may treat users, update medical-related data, maintain medical-related data, and communicate medical-related data to the transformative integration engine 102. At least some of the medical-related data may be stored local to the medical care facility 110. Further, the one or more components 106 within the medical care facility can generate medical-related data including administrative information, clinical information, and financial information as part their operations within the urgent care facility. Examples of medical care facilities include, for example, urgent care facilities, outuser facilities, hospitals, clinics, and other suitable facilities at which care is provided to users.

The medical care facility 110 can be an urgent care facility, an insta-care facility, an emergency room, or the like. For example, a doctor may update a particular electronic medical record of a user using one of the one or more components 106 or one of the one or more user devices 108 after receiving the user in the course of an emergency. In some examples, the urgent care facility may be distinct from an office of the user's primary care provider. However, in accordance with techniques described herein, the updates to the electronic medical record may be made available to the user's primary care provider, including any medical-care professionals. The update can also be saved locally in association with the user's electronic medical record, a copy (or the original) can be provided to the transformative integration engine 102, and an indication of the update can be provided to the transaction management engine 104. In some examples, the indication of the update is generated by the transaction management engine 104 as the update is provided to the transformative integration engine 102.

The medical care facility 110 can be an outuser facility (e.g., a long-term care facility, a recovery facility, a hospice facility, a rehabilitation center, a retirement home, or the like). Such a facility may In some examples, the outuser facility provide medical care to users who are not admitted to a hospital. Additionally, components within the outuser facility generate medical-related data (e.g., administrative information, clinical information, and financial information) as part their operations within the outuser facility. For example, an outuser facility may provide treatment to a user using a dialysis machine. Information pertaining to the treatment of the user using the dialysis machine can be stored locally, and a copy can then be provided to the transformative integration engine 102 such that it can coordinate storage and later retrieval of the information for use by one or more others of the one or more components 106 of the one or more user devices 108. In addition, an indication of the update to the medical-related data is provided to the transaction management engine 104 (e.g., directly or via transformative integration engine 102). The record service can also maintain updated medical-related data including electronic health record information from the outuser facility.

The medical care facility 110 can be a hospital (e.g., a type of medical care facility that provides medical, surgical, and other types of medical and nursing care). In this example, the hospital includes one or more different wards dedicated to the care and treatment of users with particular diseases, disorders, and the like. Within the wards, the hospital includes a variety of different components capable of generating medical-related data. The hospital can store a portion of the generated medical-related data for its own users locally. In some examples, users (e.g., users, doctors, etc.) may utilize the one or more components 106 and/or the one or more user devices 108 to generate such medical-related data. For example, the hospital may include, as one of its components, an MRI machine. A technician (e.g., a user) may collect one or more MRI images of a user using the MRI machine at the hospital. These MRI images, a form of medical-related data, can be stored locally, and a copy of the file can be provided to the transformative integration engine 102, which can coordinate storage and later retrieval of the information for use by one or more others of the one or more components 106 of the one or more user devices 108.

In addition, an indication of the medical-related data can be directly or indirectly provided to the transaction management engine 104. Components of the hospital can also or alternatively communicate the medical-related data to the transformative integration engine 102 or the record service. In this manner, the transformative integration engine 102 has access to updated medical-related data for the users of the hospital.

The medical care facility 110 can be a clinic (e.g., an organization of medical care professionals that provide routine medical care). In this example, the treatment offered by the clinic is devoted primarily to outusers. The clinic offers medical services options to populations in local communities and, in some examples, provides medical services to users prior to the hospital providing medical services.

The medical provider network 100 includes the one or more components 106 and the one or more user devices 108. One or more users (not shown) can access the components 106 and the user devices 108 to generate, provide, and access medical-related data within the medical provider network 100. In some examples, the medical-related data may have been received by the transformative integration engine 102 and retained for use by others of the components 106 and/or the user devices 108. The one or more users can include, for example, first responders, medical care professionals, users, or any other suitable type of user.

The first responder can include, for example, an emergency medical technician, a firefighter, a police officer, a member of the military, a designated medical volunteer, and the like. In the context of this specification, the first responder is typically dispatched or directed to the scene of an accident in order to provide medical support to victims.

In some examples, the first responder provides medical-related data to the transformative integration engine 102 using one of the one or more user devices 108 as part of responding to the dispatch. For example, in one example, the first responder arrives at a car accident, identifies a victim by one more means of identification (e.g., a driver's license number, name, address, etc.), and shares the identifying information with the transformative integration engine 102 via one of the one or more user devices 108 (e.g., a mobile phone, a radio, or other communication device). In return, the transformative integration engine 102 can facilitate the provision of medical-related data associated with the victim to the first responder. In this manner, the first responder can be informed of, for example, the medical history and other considerations while providing medical treatment to the victim.

The first responder can provide and/or receive the medical-related data via the one or more user devices 108. Thus, at least in this example, the one or more user devices 108 may operate according to a private and/or proprietary network or protocols. In other examples, the one or more user devices 108 may operate on public networks. In any case, however, the transformative integration engine 102 can have access to the one or more components and can communicate with them via a public, private and/or proprietary network or protocols. The use of one or more private and/or proprietary protocols can promote secure transfer of medical-related data.

In some examples, the one or more users can include a medical care professional and/or care provider. The medical care professional and/or care provider can provide one or more medical-related services, including, for example, examination, surgery, diagnosis, consultation, counseling, scheduling of visits, handling of protected health record information, payment handling, coordination of care, management of care, and the like. In some examples, the medical care professional is associated with the medical care facility 110. In some examples, the medical care professional is a doctor, a nurse, a surgeon, a physical therapist, a medical assistant, a facility staff person, an administrative employee, or any other person who utilizes medical-related data for treatment of users. In this example, the medical care professional utilizes some of the one or more user devices 108 to send medical-related data to, and/or receive from, the transformative integration engine 102, medical-related data. In this manner, the medical care professional can receive updates, statuses, progress, and the like relating to users of the.

In some examples, the one or more users can include a user. The user can be a user of the medical care facility 110, the first responder, and/or the medical care professional. The user can include one that has expressly or implicitly authorized the medical care facility 110, the first responder and/or the medical care professional to access and record medical-related data pertaining to services provided to the user.

Figure 2:
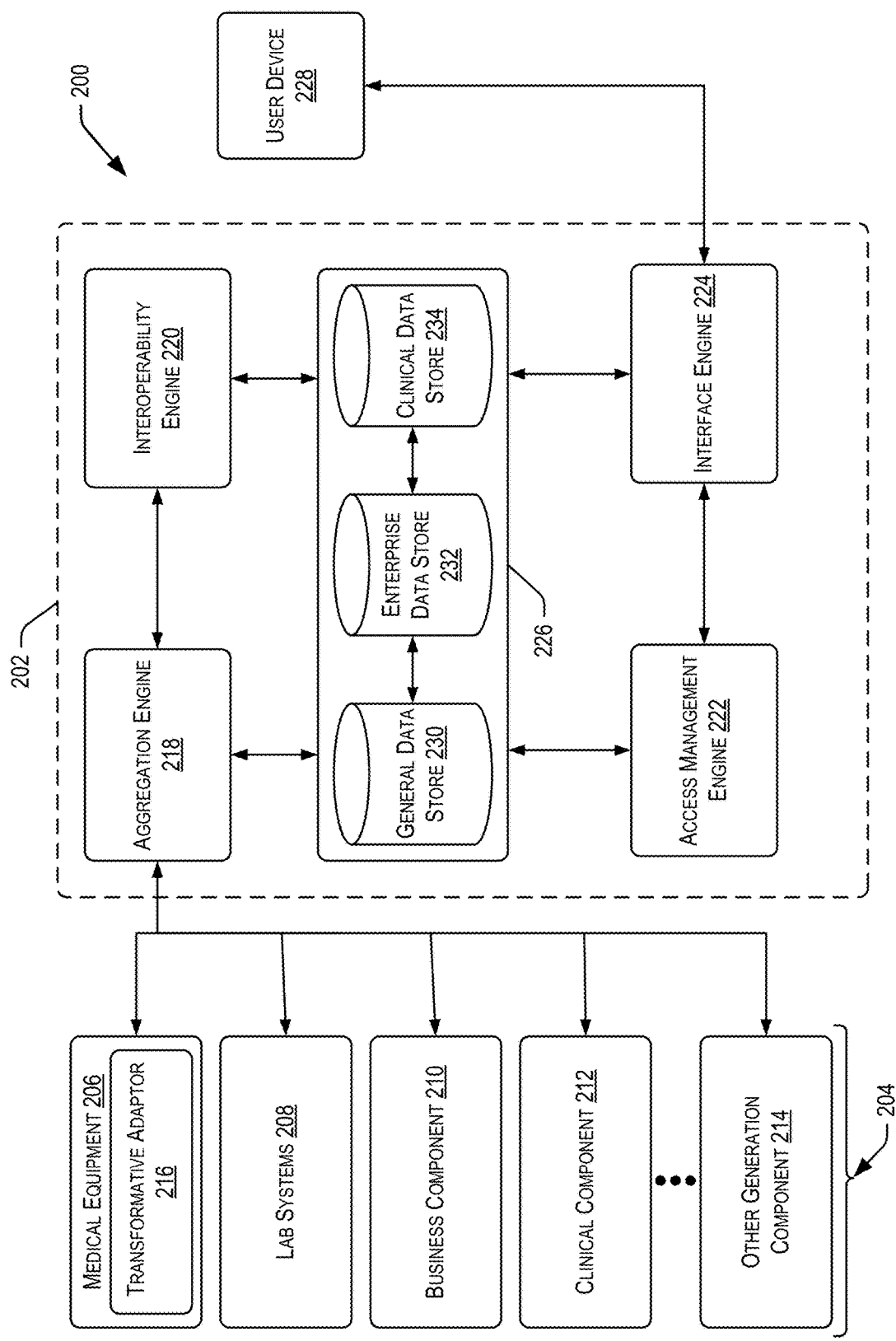
FIG. 2 is an example block diagram illustrating an environment in which techniques relating to executing reservation of resources for authorized users as described herein may be implemented, according to at least one example.

Referring next to FIG. 2, a block diagram of an example of a medical provider network 200 is shown. The medical provider network 200 includes a transformative integration engine 202. The transformative integration engine 202 is an example of the transformative integration engine 102 discussed with reference to FIG. 1. The medical provider network 200 also includes one or more generation components 204. In particular, the one or more generation components 204 includes a medical equipment component 206, a lab systems component 208, a business component 210, a clinical component 212, and other generation component 214. The one or more generation components 204 are examples of the one or more components 106 discussed with reference to FIG. 1.

Generally, the one or more generation components 204 includes any suitable device or system capable of generating medical-related data in the context of a medical provider network. For example, the other generation component 214 may include a sensor on a door in a hospital, and the medical equipment component 206 may include a sophisticated computer-controlled laser surgery device. In either case, each generation component generates some type of medical-related data. For example, the medical-related data provided by the sensor may be used to address security concerns or assessing heating, ventilating, and air conditioning (HVAC) costs for the hospital. The medical-related data provided by the laser surgery device may have been provided while operating on a user and may then be used by other doctors in the future to decide how to use the device on their own users.

As discussed in further detail herein, medical-related data generated by the one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical medical provider network includes thousands of generation components producing data in hundreds of formats. In order to harness the power that comes from such a large amount of medical-related data to make informed health care decisions, it is desirable that all, or at least a large portion of the data, is shared. Use of the transformative integration engine 202 in accordance with techniques described herein may achieve this design—making large amounts of data, in many different originating formats available to doctors, nurses, users, administrators, and third parties, via one or more interfaces.

While the one or more generation components 204 are illustrated adjacent to each other, it is understood that each may be located within one facility or that the components may be spread out among many facilities. In addition, in some examples, the one or more generation components 204 belong to different medical provider organizations.

Turning now to the medical equipment component 206, this component includes any medical machine, contrivance, implant, or other similar related article, that is intended to aid in the diagnosis, monitoring, or treatment of medical conditions. This includes, for example, diagnostic equipment, including medical imaging machines (e.g., ultrasound machines, magnetic resonance imaging (MRI) machines, positron emission tomography (PET) scanners, computed tomography (CT) scanners, and x-ray machines); therapeutic equipment (e.g., infusion pumps, medical lasers, and laser-assisted in situ Keratomileusis (LASIK) lasers); life support equipment (e.g., medical ventilators, anesthetic machines, heart-lung machines, extracorporeal membrane oxygenation (ECMO) machines, and dialysis machines) and/or medical monitors to measure user's medical state (e.g., electrocardiography (ECG), electroencephalography (EEG), blood pressure machines, and equipment for monitoring dissolved gases in the blood). Each of the above-listed components generates medical-related data that is provided to the transformative integration engine 202.

As illustrated, the medical equipment component 206 includes transformative adaptor 216. In some examples, the transformative adaptor 216 is a device that transforms, translates, converts, or otherwise adjusts output data from the medical equipment component 206. For example, a medical equipment component 206 can be a CT scanner that outputs its results in format A, but the majority of other CT scanners in the medical provider network output their results in format B. The transformative adaptor 216 may be implemented to convert or otherwise adjust the results in format A to conform closer to format B. For example, the conversion from format A to format B may be performed using a conversion rule, which may be user-define or learned. The transformative integration engine 202 may perform similar tasks as it relates to all data generated within the medical provider network 200. In this manner, the transformative adaptor 216 can perform an initial step in the process of transformation, translation, conversion, or adjustment of the output of the medical equipment component 206. In some examples, the transformative adaptor 216 is implemented in hardware, software, or any suitable combination of both. In some examples, other transformative adaptors (not shown) may be implemented within others of the one or more generation components 204. In some examples, the medical equipment component 206 may not include the transformative adaptor 216.

The lab systems component 208 includes any suitable medical laboratory equipment or system that is intended to analyze material related to user care. This includes, for example, medical laboratory equipment that analyzes blood, urine, and genes; electric microscopes; ultracentrifuges; data collection devices, including Kymographs, sensors connected to a computer to collect data; monitoring devices; computers used by clinicians to report results of lab tests, and other similar medical laboratory equipment. Each of the above-listed components generates medical-related data that is provided (directly or indirectly) to the transformative integration engine 202. The provided data can further include an identification of a user and/or other user-pertinent information (e.g., actual or suspected diagnosis and/or demographic information).

The business component 210 includes any suitable computing devices used for business-related purposes with respect to the medical provider network 200. For example, the business component 210 can be configured to receive inputs by employees of a hospital to prepare medical-related data including business-related data relating to eligibility and registration of users, scheduling and throughputs, general supply chain materials management, pharmacy supply chain materials management, human resources, financial documentation and logging, building operations, information technology systems, marketing, budgeting, and other similar business-related purposes. In some examples, the business-related information is auto-generated or populated by the business component 210. At least a portion of such information is provided to the transformative integration engine 202.

The clinical component 212 includes any suitable computing device used in research, treatment, and care of users. For example, the clinical component 212 is used to generate medical-related data including clinical data, which may further include an identification of a user and/or other user-pertinent information. For example, the clinical component 212 is used by nurses, technicians, doctors, and/or other individuals associated with a hospital, clinic, lab, or other similar entity to prepare clinical data. Clinical data includes, for example, output relating to computerized physician order entry (CPOE), protected health information for users (i.e., a subset of medical-related data), dictations, lab results, lab requests, lab tests, orders for medical supplies, intake and checkout of users, medical reports, clinical tests, clinical documentation, and other similar clinical information. At least a portion of such information is provided to the transformative integration engine 202. In some examples, the clinical data is auto-generated or populated by the clinical component 212. The clinical component 212 and the business component 210 are often selected from a similar group of computing devices.

Each of the one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting medical-related data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with the transformative integration engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or the transformative integration engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive medical-related data from one or more sensors. For example, a particular port may include an interface for receiving data collected from an ultrasound machine. The sensors may be any suitable type of sensor to capture data. Such captured data may be shared with the transformative integration engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the medical-related data provided by the component or the user device located at the geographic location.

The transformative integration engine 202 includes an aggregation engine 218, an interoperability engine 220, an access management engine 222, an interface engine 224, and a data store 226. Generally the aggregation engine 218 is configured to collect medical-related data of different formats generated by the one or more generation components 204. The aggregation engine 218 may also be configured to perform one or more operations on the collected data. For example, the aggregation engine 218 may tag data, log data, perform protocol conversion, and may support one-to-many communications. The collection may be asynchronous. In some examples, the medical-related data has been saved locally in connection with the one or more generation components 204 in many different formats having many different data structures.

The aggregation engine 218 is configured to receive such diverse (or, in other embodiments, uniformly formatted) data and provide it to the interoperability engine 220. The interoperability engine 220 is configured to perform one or more operations on the received medical-related data and store it in the data store 226. For example, the interoperability engine 220 may perform semantic tagging and indexing of medical-related data. This may include extracting field values from data, categorizing data (e.g., by type of data, characteristic of user, location of medical care facility, characteristic of medical care facility, and the like), anonymizing or partially-anonymizing data, and the like. The interoperability engine 220 may also include a high availability cache, an alerts engine and a rules engine. In some examples, the interoperability engine 220 operates synchronously.

From the interoperability engine 220, medical-related data flows to the data store 226. The data store 226 (and any other data store discussed herein) may include one or more data stores, which may be distributed throughout two or more different locations (e.g., present on different devices, which can include devices of different entities and/or a cloud server). In some examples, the data store 226 includes a general data store 230, an enterprise data store 232, and a clinical data store 234. Within each of the data stores 230, 232, and 234 is stored medical-related data. Depending on the structure of the particular data store, certain data stores may include rules for reading and writing. The data stores 230, 232, and 234 may include records, tables, arrays, and the like, which may be relational or non-relational. Depending on the data store, records for individual users, results of clinical studies, business and analytics information, output data from the one or more generation components 204, and the like may be retained. The data within the data stores 230, 232, and 234 include elements or tags such that a particular data (e.g., for a single user, doctor, diagnosis, type of doctor, type of treatment, users matching a criteria, and the like) can be retrieved.

The access management engine 222 is configured to manage access to features of transformative integration engine 202, including access to the medical-related data retained in the data store 226. For example, the access management engine 222 may verify that a user device such as user device 228 is authorized to access the data store 226. To verify the user device 228, the access management engine 222 may require that a user of the user device 228 input a username and password, have a profile associated with the medical provider network, have paid a subscription fee associated with access to the data store 226, and the like. The access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

The interface engine 224 is configured to retrieve the data from the data store 226 and provide one or more interfaces for interacting with elements of the transformative integration engine 202. For example, the interface engine 224 includes an interface by which an application running on user device 228 can access portions of data within the data store 226

Figure 3:
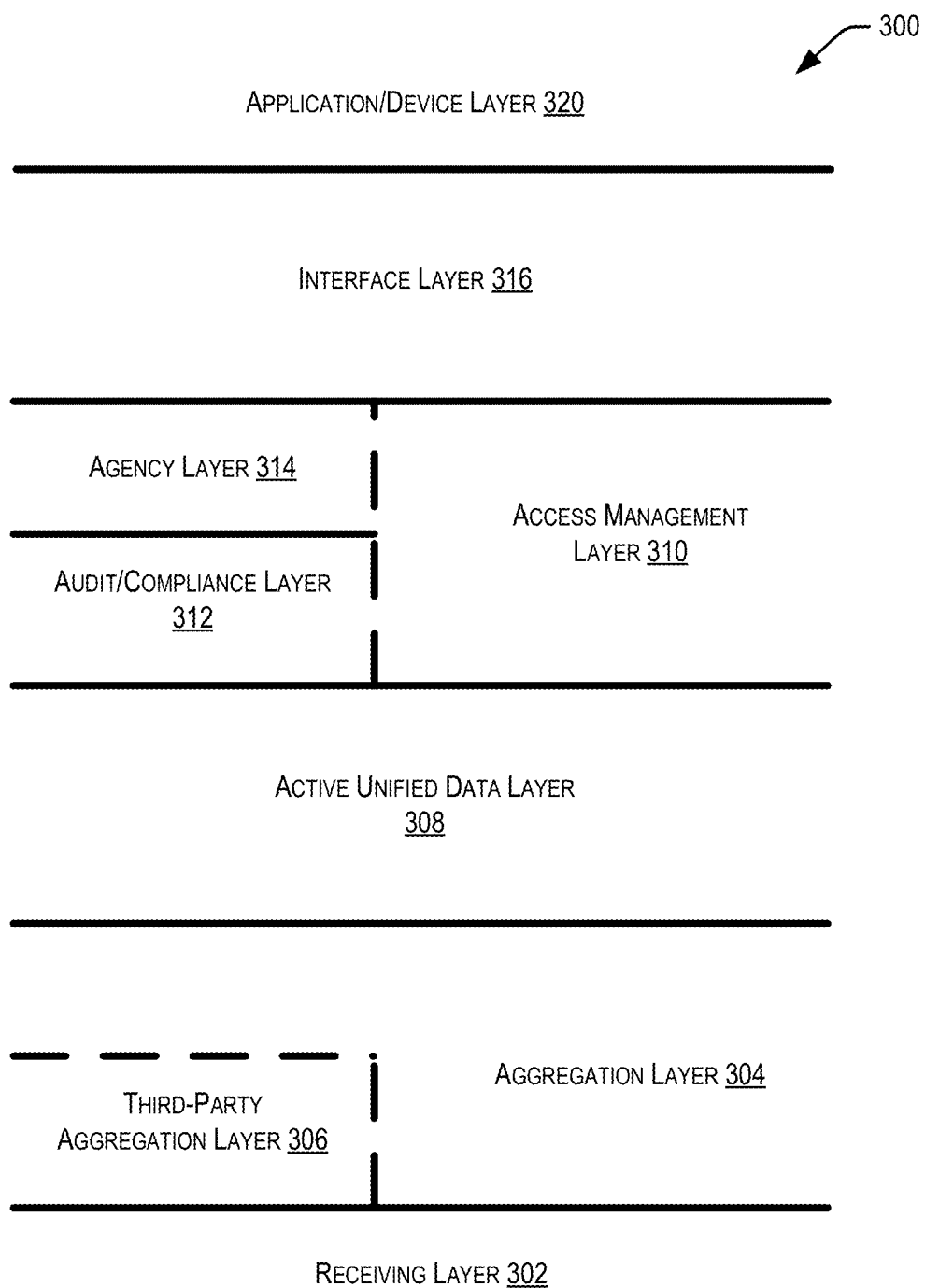
FIG. 3 is an example schematic model illustrating an a network communication model in which techniques relating to executing reservation of resources for authorized users as described herein may be implemented, according to at least one example.

Turning next to FIG. 3, a medical architecture stack 300 is shown. In some examples, techniques relating management of medical-related data are implemented in accordance with the medical architecture stack 300. And while the medical architecture stack 300 is illustrated as having a particular structure, it is understood that other structures, including those with more or less layers than illustrated, is within the scope of this specification. In some examples, the medical architecture stack 300 is implemented across a medical provider network having a plurality of systems belonging to the same medical provider organization or spread across different medical provider organizations. Thus, the medical architecture stack 300 can be used to integrate different systems of different organizations, entities, and the like and to provide a fluid sharing of information among elements within the medical provider network and without the medical provider network. In some instances, a multi-layer part of the medical architecture stack 300 is implemented at a single system or device within a medical provider network.

The different layers of the medical architecture stack 300 will be described generally with reference to FIG. 3 and in detail with reference to subsequent figures. The medical architecture stack 300 includes a receiving layer 302 as the bottom-most layer. The receiving layer 302 includes receiving medical-related data from elements that share medical-related data with other elements within an aggregation layer 304. For example, as detailed herein, the receiving layer 302 can include receiving medical-related data from generation components that generate medical-related data. As such, the receiving layer 302 is where medical-related data that has been created is received. In some examples, the data within the receiving layer 302 may be in its raw formats. For example, output from an MRI machine may be received within the receiving layer 302. The output may then be transmitted to the aggregation layer 304. In some examples, components of the receiving layer 302 may have complimentary layers to facilitate data transfer. For example, the components may include a data generation and/or a data transmission layer for providing data to the receiving layer 302.

Elements of the aggregation layer 304 aggregate the medical-related data generated by the elements of the receiving layer 302. For example, the elements of the aggregation layer 304 may include aggregation engines that collect data from generation components located within the receiving layer 302. Such aggregation may be performed periodically, in response to a user request, according to a schedule, or in any other suitable manner. In some examples, data of the aggregation layer 304 may be aggregated according to input and/or rules and may aggregate across records pertaining to, e.g., a same medical care professional, medical care facility, entity, time period, user characteristic (e.g., demographic characteristic or condition), user health outcome, and any other suitable input and/or rules. Exemplary data being aggregated can include, e.g., diagnosis for particular users and/or user groups, test results, treatment parameters or characteristics, health outcomes (e.g., side effect occurrence, mortality, readmissions, sepsis, etc.), pharmacy orders, user record data, and the like. The aggregation may include compiling the data, generating a distribution, generating a statistic pertaining to the data (e.g., average, median, extremum or variance), converting the data, transforming the data to different formats, and the like.

Next, the medical architecture stack 300 includes an active unified data layer 308. Elements of the active unified data layer 308 receive medical-related data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of the active unified data layer 308 may receive information collected or generated within the aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within the active unified data layer 308.

The medical architecture stack 300 also includes an access management layer 310, which can include an audit/compliance layer 312 and/or an agency layer 314. The access management layer 310 includes elements to manage access to the medical-related data. For example, the access management layer 310 may include elements to verify user login credentials, IP addresses associated with a user device, and the like prior to granting the user access to data stored within the active unified data layer 308.

The audit/compliance layer 312 includes elements to audit other elements of the medical architecture stack 300 and ensure compliance with operating procedures. For example, this may include tracking and monitoring the other elements of the access management layer 310.

The agency layer 314 includes an access location (e.g., a virtual private network, a data feed, or the like) for elements of agencies that are interested in the operations of the medical provider network in which the medical architecture stack 300 is implemented. For example, the agency layer 314 may allow a governmental entity access to some elements within the medical architecture stack 300. This may be achieved by providing the governmental entity a direct conduit (perhaps by a virtual private network) to the elements of the access management layer 310 and the medical-related data within the active unified data layer 308. The audit/compliance layer 312 and the agency layer 314 are sub-layers of the access management layer 310.

The medical architecture stack 300 also includes interface layer 316. The interface layer 316 provides interfaces for users to interact with the other elements of the medical architecture stack 300. For example, medical care providers, users, medical care administrators, and others belonging to the medical provider network may utilize one or more user devices (interacting within the application/device layer 320) to access the medical-related data stored within the active unified data layer 308. In some examples, the users may be unrelated to the medical provider network (e.g., ordinary users who are not users, family members of users, research universities, for profit and non-profit research organizations, world health care organizations, disaster relief organizations, and the like) and may use applications (not shown) to access the elements within the medical architecture stack 300 via one or more interfaces (e.g., to access medical-related data stored within the active unified data layer 308). Such applications may have been developed by the medical provider network or by third-parties Finally, the medical architecture stack 300 includes application/device layer 320. The application/device layer 320 includes user devices and applications for interacting with the other elements of the medical architecture stack 300 via the elements of the interface layer 316. For example, the applications may be web-based applications, user portals, doctor portals, mobile applications, widgets, and the like for accessing the medical-related data. These applications may run on one or more user devices. The user devices may be any suitable user device as detailed herein.

Figure 4:
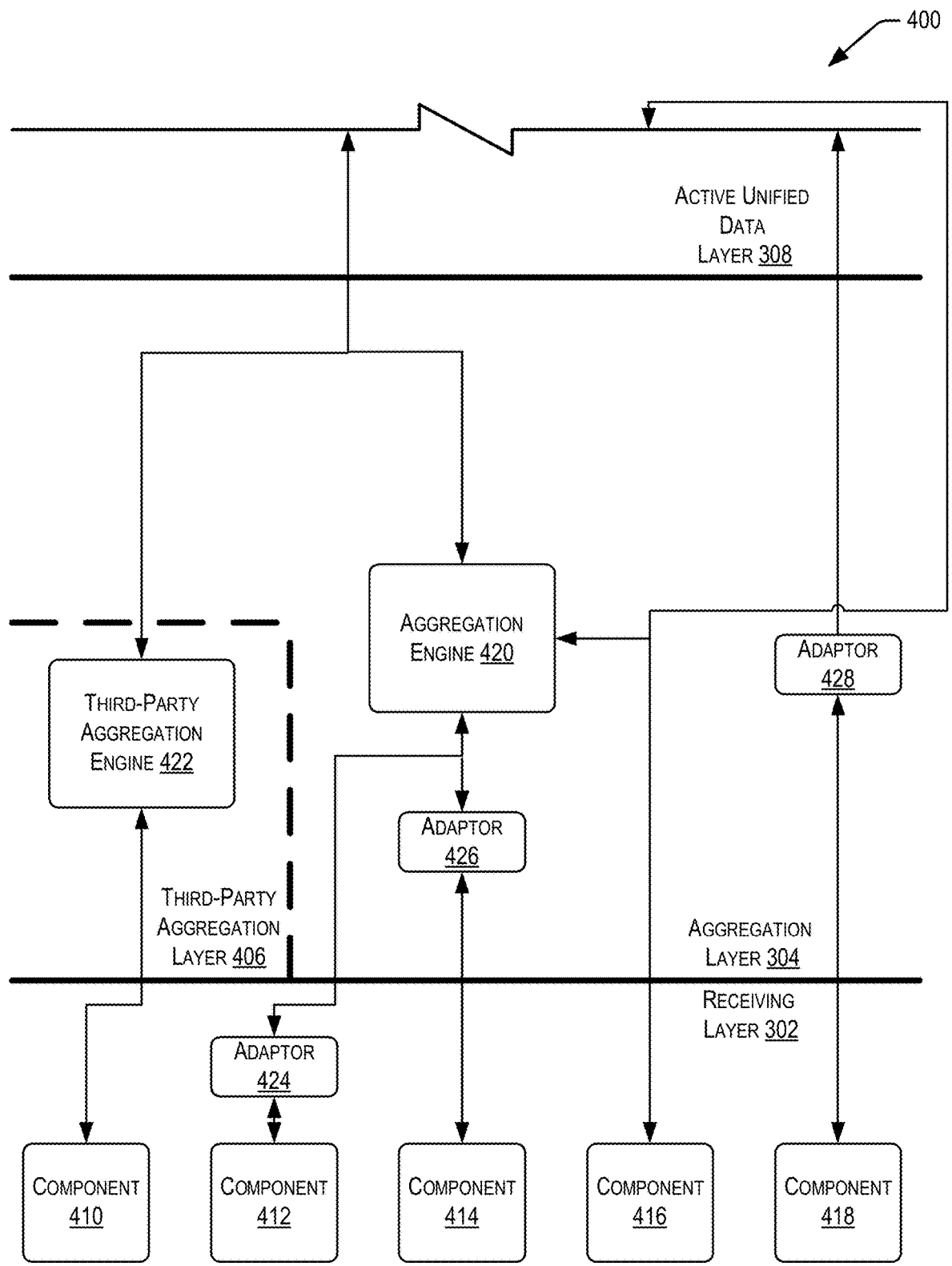
FIG. 4 is an example schematic model illustrating an aspect of the network communication model of FIG. 3 in more detail.

Turning next to FIG. 4, a diagram 400 is shown that depicts a portion of the medical architecture stack 300 according to an embodiment of the invention. In particular, the diagram 400 includes the receiving layer 302, the aggregation layer 304, the third-party aggregation layer 306, and a portion of the active unified data layer 308. The receiving layer 302 receives data from one or more components 410-418. The components 410-418 are examples of the one or more generation components 204. The components 410-418 may be spread across multiple medical care facilities within a single or multiple medical provider organizations. For example, the component 410 may be located at a hospital, the component 412 may be located at a clinic, the component 414 may be located at urgent care facility, and so forth. Additionally, the hospital may belong to a first medical provider organization, while the clinic may belong to a second medical provider organization, both of which or part of which may belong to the same medical provider network. In some examples, the components 410-418 may include complimentary layers to facilitate data transmission. For example, the components 410-418 may include a transmission layer, generation layer, and/or a receiving layer to communicate data at the receiving layer 302 and, in some examples, receive data from the receiving layer 302.

In some instances, two or more of the components 410-418 generate medical-related data according to different formats. The medical-related data can then be transformed, translated, or otherwise adjusted before an aggregation engine 420 (e.g., the aggregation engine 218) or a third-party aggregation engine 422 (e.g., the aggregation engine 218) collects the medical-related data. In some examples, the adjustment takes place within the receiving layer 302. Thus, an adaptor 424 is associated with the component 412 located in the receiving layer 302. The adaptor 424 is an example of the transformative adaptor 216. The adaptor 424 is implemented, as appropriate, in hardware, software, or any suitable combination of both. For example, the transformative adaptor 216 may be a bolt-on adaptor that adjusts medical-related data as such data leaves the component 412.

Other adaptors, such as adaptor 426 and adaptor 428, are implemented within the aggregation layer 304. These adaptors can function in a similar manner as the adaptor 424. In some examples, the medical-related data provided by the component 414 is transmitted through adaptor 426 prior to being directed to the aggregation engine 420. The medical-related data provided by the component 416 is transmitted through the aggregation layer 304 and/or enters the aggregation engine 420 without having first traveled through an adaptor. The medical-related data provided by the component 418 is transmitted through the aggregation layer 304 and through adaptor 428. In some examples, the component 418 provides for streaming of medical-related data. The medical-related data provided by the component 410 is transmitted directly to the third-party aggregation engine 422.

The aggregation engine 420 and the third-party aggregation engine 422 function in a similar manner. In some examples, the third-party aggregation engine 422 is operated by a different entity than the entity that operates the aggregation engine 420 and may belong to different medical provider organizations or a different medical provider network. This may be because the medical-related data collected by the third-party aggregation engine 422 differs in some way from the medical-related data collected by the aggregation engine 420. In any event, the aggregation engine 420 is configured to perform integration of medical-related data, including generic integration. For example, the aggregation engine 420 performs one or more operations on medical-related data including tagging, logging, and protocol conversion. The aggregation engine 420 also supports one-to-many communications of medical-related data. In some examples, medical-related data flows between the aggregation engine 420, the third-party aggregation engine 422, and some of the components 410-418 and elements of the active unified data layer 308.

Figure 5:
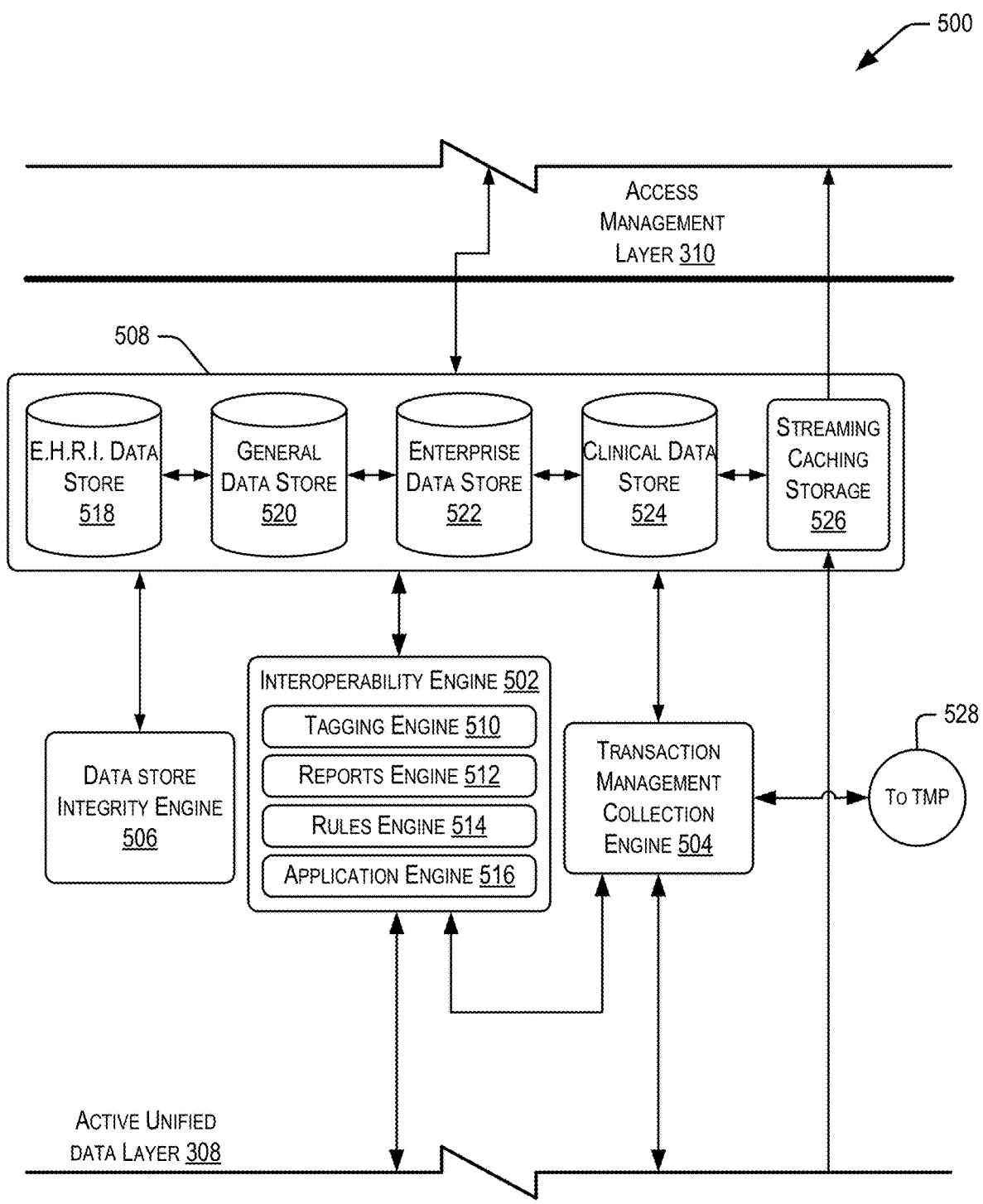
FIG. 5 is an example schematic model illustrating an aspect of the network communication model of FIG. 3 in more detail.

Referring next to FIG. 5, a diagram 500 is shown that depicts a portion of the medical architecture stack 300 according to an embodiment of the invention. In particular, the diagram 500 includes the active unified data layer 308 and a portion of the access management layer 310. The active unified data layer 308, as illustrated in the diagram 500, includes an interoperability engine 502 (e.g., the interoperability engine 220), a transaction management collection engine 504, a data store integrity engine 506, and a data store 508 (e.g., the data store 226). Generally, the interoperability engine 502 receives medical-related data from elements within the aggregation layer 304 (e.g., from the aggregation engine 420) and performs one or more operations with respect to the medical-related data. The interoperability engine 502 also facilitates storage of at least a portion of the processed information in the data store 508.

The transaction management collection engine 504 is implemented as part of the transaction management engine 104. The transaction management collection engine 504 is configured to generate message indicators identifying flows of data by and between elements of a medical provider network implemented using the techniques described herein. The flows of information include messages which include medical-related data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including medical-related data are transmitted from the aggregation layer 304. The table may be stored in association with the transaction management platform 528.

In some examples, the table also includes information for tracking the progress of the message from an origination node to a destination node. For example, typically when a message (e.g., any communication of data) is first received by the transformative integration engine 102 (e.g., the interoperability engine 502), the transaction management engine 104 (e.g., the transaction management collection engine 504 of the transaction management engine 104) may generate a unique identifier for the message in order to track that message as it moves throughout the medical provider network. The unique identifier may be included in the header of the message such that when the next node (e.g., component, device, server, etc.) after the transformative integration engine 102 receives the message, that node can report back to the transaction management engine 104 that it saw the message. In this manner, the transaction management engine 104 may enable end-to-end tracking of messages for the life of the message. In one example, the messages are pharmacy orders. The pharmacy orders may be generated by a user entering in the orders at one of the components. The orders may be received by the transformative integration engine 102 and integrated into the system. In some examples, the transaction management engine 104 may be notified that the orders have been received and may therefore be configured to generate message IDs for each order. These message IDs may then be associated with each of the orders. As the orders continue to move throughout the medical provider network (e.g., away from the transformative integration engine 102), the transaction management engine 104 may be track their movement using the message IDs. If one of the orders does not make it to its destination, the transaction management engine 104 (or part of the transaction management platform 528) may determine why the order was stopped. In some examples, this cause may be hardware related (e.g., an unplugged Ethernet cable, a broken router, etc.), software related (e.g., a router routing to the wrong location), or any other reason for orders not arriving at their correct destination.

In some examples, the transaction management engine 104 (e.g., the transaction management collection engine 504 of the transaction management engine 104) may receive the message and/or message identifier directly from one of the components 410-418. For example, one of the components 410-416 may be configured to generate the unique message identifier and/or communicate directly with the transaction management engine 104. The message also may travel via one or more intermediate odes on its way to the destination node. In some examples, a node is a component such as the components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, the transaction management collection engine 504 provides unique message identifiers to other elements of the medical provider network to monitor the messages as they move throughout the medical provider network. The transaction management collection engine 504 also provides a portion of the unique message identifiers to a transaction management platform (indicated by circle 528) for further analysis of the message identifiers. Such analysis may include reconciliation of lost messages, latency reporting, audit management and compliance, and other such analyses.

As mentioned previously, the interoperability engine 502 is configured to store medical-related data in the data store 508. A plurality of sub-engines 510-516 of the interoperability engine 502 are configured to perform operations relating to storing medical-related data in the data store 508.

The interoperability engine 502 includes a tagging engine 510 configured to perform semantic tagging and indexing of medical-related data. The tagging engine 510 therefore is configured to receive medical-related data, read metadata associated with the medical-related data, semantically scan the content of the medical-related data, and associate one or more tags with the medical-related data. The tagging engine 510 may therefore have access to hundreds, thousands, or even more possible tags. These tags may have been input by users, learned, pre-defined, generated by outside third-party mapping sources, and/or gathered from other components and/or data stores of the medical provider network. For example, if the medical-related data is a medical chart for a cancer user, the tagging engine may be configured to read any metadata associated with the chart to determine which tags may be appropriate to associate with the chart. From the metadata the tagging engine 510 may determine that the chart is for a cancer user by reading metadata indicating that an author field is populated with the name of an oncologist who prepared the medical chart. The tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the medical care provider or medical care facility where the data originated, and other similar fields. The tags may be stored in association with the medical-related data (e.g., the chart) and/or may be stored independent from the medical-related data but include an identifier such that when searching tags the medical-related data may be capable of population.

Continuing with the example from above, if the medical-related data is a medical chart for a cancer user, the tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by the tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of medical-related data. This meaning and/or context may assist the tagging engine 510 to determine one or more tags to associate with the medical-related data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, the tagging engine 510 may also index portions of the medical-related data within one or more data stores of the data store 508. In some examples, the such indexing may be based in part on the selected tags.

The interoperability engine 502 also includes an reports engine 512 configured to generate one or more reports or alerts based on medical-related data. For example, the reports engine 512 may generate reports when certain types of medical-related data are received or when medical-related data with certain characteristics is received. The reports engine 512 may also generate alerts. The reports and/or alerts generated by the reports engine 512 may be outputted in the form of one or more communications to an administrator, an authorized user, or other similar user via a user device. Such communications include, for example, signals, sirens, electronic notifications, popups, emails, and the like. Content of such communications may include information characterizing a care provider's or institution's performance in providing care, efficiency and/or user outcomes; identifying concern user-data patterns; identifying losses of medical-related data; and the like. In some examples, the content is presented in the form of one or more documents, tables, figures, charts, graphs, and the like. For example, the reports engine 512 may output a report to a hospital administrator indicating the user outcomes for the hospital for the last year. This report may be presented in the form of a graph.

The interoperability engine 502 also includes a rules engine 514 configured to create and manage business rules, health-response rules, alert/reports rules, data-formatting rules, data-sharing rules, transmission rules, aggregation rules, user authorization rules, law-based rules, and other similar rules. Such rules may be user-defined, fixed, learned by elements of the medical provider network, and any combination of the foregoing. For example, a business rule may be defined by a hospital administrator and relate to supply chain management and visualization and optimization of planning and scheduling. The rules can apply across different medical care facilities, medical conditions, user types, geographic areas, and/or entities. Finally, the interoperability engine 502 includes an application engine 516 configured to provide service-oriented architecture web services.

The data store 508 includes an electronic health record information (EHRI) data store 518 ("the record data store 518"), a general data store 520, an enterprise data store 522, a clinical data store 524, and a streaming caching storage 526. While the data store 508 is illustrated as including a fixed number of data stores and storage elements, it is understood that the data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables (e.g., pertaining to a similar medical condition, treatment, physician or geographical region) but that differ in one or more other variables (e.g., institution affiliation). Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within the record data store 518 is retained medical-related data including electronic health record information. In some examples, the information within the record data store 518 is organized according to user identifying information. Thus, the record data store 518, in some examples, includes individually identifiable information. But it may also include de-identified information.

Within the general data store 520 is retained medical-related data. The medical-related data may be stored in a relational database format or in any other suitable format. Thus, the data within the general data store 520 may be retained in a data structure that includes one or more tables capable of accessing each other. The general data store 520 includes certain types of clinical information. For example, the general data store 520 may include orderables and labs. In some examples, the general data store 520 includes medical-related data, including medical record information associated with users, user insurance information, demographic information of the users, and at least some financial information of the users. In some examples, the general data store 520 includes all medical-related data needed for clinical decision making as discussed herein. In some examples, the general data store 520 includes a subset of the information that is included in the enterprise data store 522.

Within the enterprise data store 522 is retained medical-related data in a relational database format. Thus, the data within the enterprise data store 522 may be retained in a data structure that includes one or more data structures (e.g., tables) capable of accessing each other. The enterprise data store 522 is an example of an enterprise data warehouse. In the enterprise data store 522 is joined many different types of medical-related data. For example, clinical, financial, and administrative information are stored in the enterprise data store 522. In some examples, the enterprise data ware house 522 includes medical-related data pertaining to clinical decision making as discussed herein and other medical-related data typically used by conventional business concerns. Thus, in the enterprise data ware house 522 may be combined clinical decision making information and business operations information. For example, the enterprise data warehouse 522 may include financial information, supply chain information, business units organization information, clinical organization information, human resources information, and any other suitable type of information relevant to the operations of a medical care organization as a business concern, whether non-profit or for profit.

Within the clinical data store 524 is retained medical-related data in a non-relational database format. Thus, the data within the clinical data store 524 may be retained in a structure other than tables. Such structure may be appropriate for large and complex data sets including medical-related data. In some examples, the clinical data store 524 (or any other data store) may be a unified system for clinical information, which may include: a document-centric, schema-agnostic, structure-aware, clustered, transactional, secure, database server with built-in search and a full suite of application services. An example of such a unified system may be Marklogic. The clinical data store 524 can support data aggregation, data organization, data indexing, data tagging and mapping to semantic standards, concept matching, concept extraction, machine learning algorithms, concept discovery, concept mining, and transformation of personal medical record information. In some examples, clinical data store 524 includes medical-related data pertaining to clinical decision making (similar to the general data store 520) as discussed that is organized and accessed in a different manner. For example, the medical-related data within the clinical data store 524 may be optimized for providing and receiving information over one or more health information exchanges. In some examples, such organization may mean that less demographic information is associated with each user, or only a portion of financial information is associated with each user. In some examples, the clinical data store 524 includes a subset of the information that is included in the enterprise data store 522.

Finally, in some examples, the streaming caching storage 526 is a streaming data cache data store. As discussed previously, certain components of the components 410-418 may support streaming data to other components or user devices. The streaming caching storage 526 is a location where streaming data can be cached. For example, assume that the component 418 is an MRI machine operated by a technician in hospital A and that a doctor using a computer in hospital B desires to view a live of substantially live stream of the MRI results. The component 418 can send a portion of data to the streaming caching storage 526 which can retain the portion of the data for a certain period of time (e.g., 1 day). Thus, the streaming caching storage 526 is configured to cache data that can be streamed.

The diagram 500 also includes data store integrity engine 506. In some examples, the data store integrity engine 506 is configured to ensure integrity of the information within the data store 508. For example, the data store integrity engine 506 applies one or more rules to decide whether information within all or part of the data store 508 should be scrubbed, removed, or adjusted. In this manner, confidence is increased that the information within the data store 508 is accurate and current.

Figure 6:
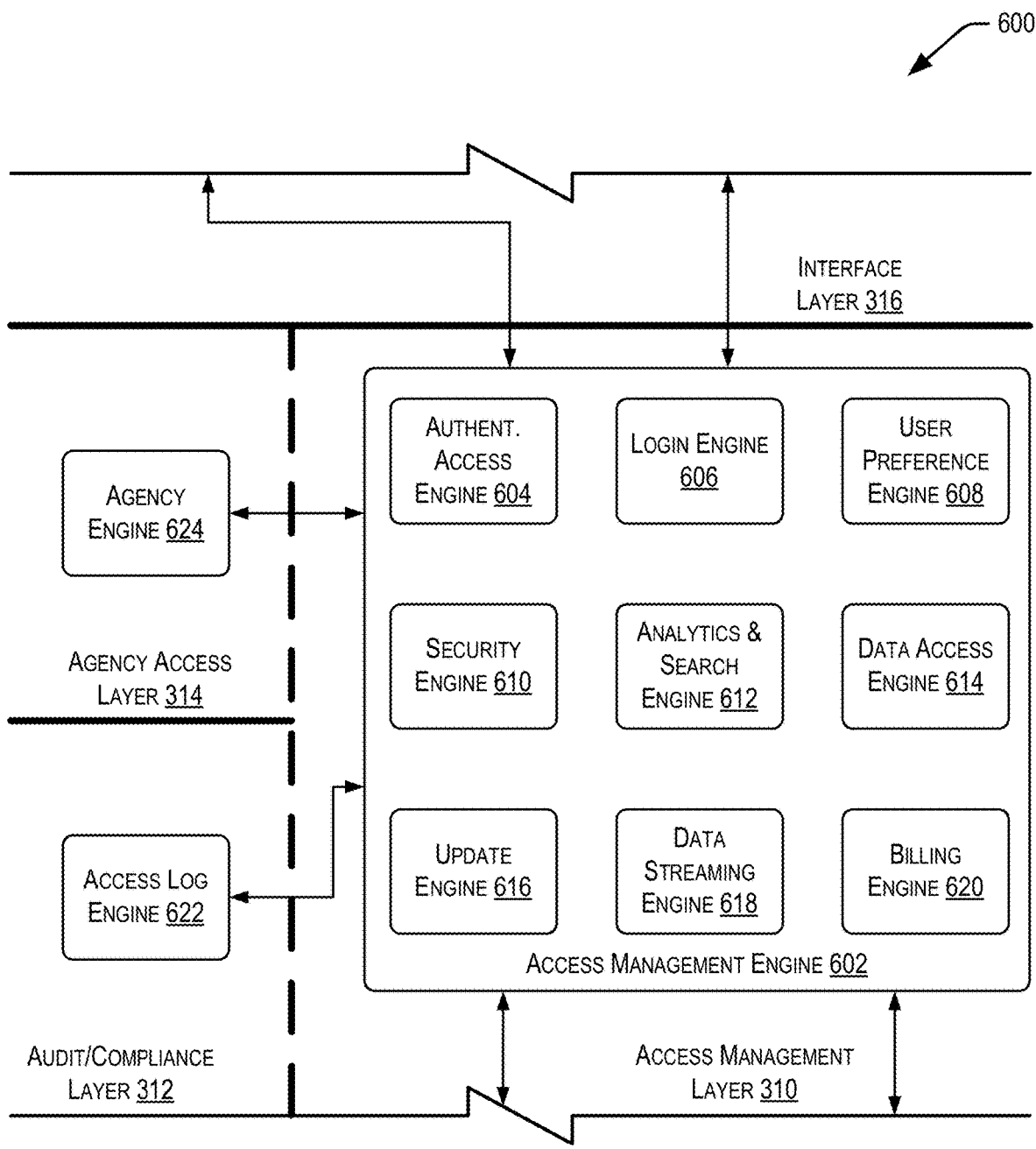
FIG. 6 is an example schematic model illustrating an aspect of the network communication model of FIG. 3 in more detail.

FIG. 6 shows a diagram 600 which depicts a portion of the medical architecture stack 300 according to an embodiment of the invention. In particular, the diagram 600 includes the access management layer 310, the audit/compliance layer 312, the agency layer 314, and a portion of the interface layer 316.

The access management layer 310, as illustrated in the diagram 600, includes an access management engine 602. The access management engine 602 is an example of the access management engine 222. Generally, the access management engine 602 can be configured to manage access to elements of the transformative integration engine 202 by different components, applications, and user devices.

The access management engine 602 within the access management layer 310 also provides functionality similar to an operating system. For example, the access management engine 602 includes a plurality of engines configured to manage different aspects of interacting with elements of the medical provider network. For example, a user who desires to access portions of medical-related data retained in the data store 508, may do so by interacting with the access management engine 602 using one or more applications (not shown). Thus, the access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, a streaming data engine 618, and a billing engine 620. The different engines of the access management engine 602 can define routines, protocols, standards, and the like for interacting with elements of the medical provider network.

Beginning first with the authentication access engine 604, the authentication access engine 604 evaluates the rules and conditions under which users may access elements of the medical provider network; in particular, the conditions under which users may access medical-related data within the data store 508. These rules and conditions may be user-defined (e.g., by an administrator or reviewer), learned over time, and/or may be dynamically updated and/or evaluated based on characteristics of the user or the user's device attempting to access the medical provider network. The rules and conditions may indicate the types of users who have particular types of access within the medical provider network. For example, hospital administrators may have a different type of access from a user. The type of access may also relate to the degree to which data is identified/de-identified. For example, a doctor to whom a release has been given, may have access to all of a user's medical record. Similarly, a researcher may have access to the records for many users, so long as the records are do not include identifying information. In some examples, a user desiring access to medical-related data provides certain identifying information and the authentication access engine 604 authenticates an identity of the user. For example, suppose the user is a doctor and the access is to medical charts for one of the doctors users. To authenticate the doctor's identity, he or she provides identifying information and once validated can be granted access to elements of the medical provider network where such information may be stored.

The login engine 606 evaluates the rules and conditions under which users are able to log in to the medical provider network or access applications associated with the medical provider network. These rules and conditions may be user-defined (e.g., by an administrator), learned over time, and also may be dynamically updated and/or evaluated based on characteristics of the user or the user's device attempting to access the medical provider network. Thus, while the authentication access engine 604 evaluates the rules to determine which users may access the medical provider network, the login engine 606 evaluates the particular credentials, profiles, etc. of the users. For example, the login engine 606 can confirm that an entered username (e.g., and password), provided biometric data or code or identifier in a scanned tag or badge matches that in an authorized user data structure.

The login engine 606 evaluates one or more user profiles associated with each authenticated user. In some examples, a user profile includes a username, password, and other information associated with the user. For example, a user profile may indicate characteristics about the user (e.g., that the user is user belonging to a particular doctor, that the user is an employee belonging to a particular medical care facility, that the user is a vendor seeking access to certain portions of the medical provider network, that the user is a doctor having a particular specialty, that the user is a scheduler who belongs to a clinic, and other characteristics).

The user preference engine 608 evaluates the rules and conditions under which user are able to store and update one or more user preferences corresponding to access of the medical provider network or access to applications associated with the medical provider network. These rules and conditions may be user-defined (e.g., by the user or an administrator), and may include rules for default preferences. For example, using the user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

The security engine 610 evaluates the rules and conditions for ensuring the security of access to the elements of the medical provider network. In some examples, these rules and conditions are determined by administrators of the medical provider network. In some examples, the security engine 610 provides a plurality of computer virus protection services. These services can be called up and implemented when accessing the medical provider network or accessing applications associated with the medical provider network. The rules and conditions may be based on roles, based on profiles, based on domains, and any other suitable security configuration. For example, because the medical provider network may include sensitive medical-related data, the security engine 610 may enforce a domain-based rule that protects certain sensitive information (e.g., identifying information).

The analytics and search engine 612 evaluates the rules and conditions under which users can search for data within the medical provider network and access analytics relating to the medical provider network. In some examples, these rules and conditions are user-defined or learned over time in accordance with search engine optimization techniques. For example, the analytics and search engine 612 is used to search within the data store 508 for particular medical-related data. The analytics and search engine 612 supports any conventional searching algorithms. For example, the search engine 612 can be used to search within various fields and potential field values (e.g., Hospital field, state field, specialty field, diagnosis field, health outcome field, doctor field). In some examples, search engine 612 can provide analytics, such as statistics, graphs, distributions and/or comparative analysis pertaining to particular entities and/or medical characteristics. Such information may be selected by a user and presented on a user interface.

The data access engine 614 evaluates the rules and conditions under which users may operation in order to access particular medical-related data within the data store 508. In some examples, these rules and conditions are user-defined or learned over time. For example, the data access engine 614 may indicate the routines, subroutines, or other logic needed for an application to access certain portions of the data store 508. For example, while the authentication access engine 604 and the login engine 606 may manage which users can access parts of the medical provider network, the data access engine 614 may manage how authenticated users access data within the data store 508. To this end, the data access engine 614 may enforce and/or evaluate certain rules managing how users access different components of the medical provider network. In some examples, the data access engine 614 may be used to actually access data within the data store 508 (e.g., extract, download, or otherwise access). In some examples, the data access engine 614 may define procedures, protocols, and the like for accessing data. The protocols and procedures for accessing the data access engine 614 (like the other engines of the access management engine 602) may be provided to developers in the form of a software development kit (SDK). SDKs may enable developers write applications that can effectively communicate with elements (e.g., the data store 508) of the medical provider network. In particular, applications that can access a portion of the medical-related data stored within the active unified data layer 308.

The update engine 616 evaluates the rules and conditions for providing updates to other engines within the access management engine 602, plug-ins for applications that access the medical provider network, and for other similar elements of the medical provider network. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

The streaming data engine 618 defines the rules and conditions for enabling streaming of medical-related data between components and user devices of the medical provider network. For example, the streaming data engine 618 may enable the component 414 to stream medical-related data. Streamed data may include live or substantially live audio or video feeds, results of medical tests, output from medical equipment or devices, and any other suitable type of medical-related data capable of being streamed. In some examples, the data may be streamed to other components or user devices within the medical network or outside the medical network. In order to establish a streaming transmission, the streaming data engine 618 may identify a streaming destination and a streaming origin. Next, the streaming data engine 618 may pair the two and enable streaming. This may include allocated bandwidth within one or more network devices associated with the medical provider network. The streaming data engine 618 may also adjust the quality of the streaming data based on the availability of bandwidth. In some examples, the streaming data engine 618 may receive incoming streams (and continuously present the stream or monitor for particular data (e.g., exceeding a threshold, exhibiting an above-threshold change, having a particular value)).

The billing engine 620 evaluates the rules and conditions under which applications and users that access the medical provider network are billed. For example, the billing engine 620 may include a variety of different charging rules to be applied to applications and users. An example rule indicates that applications or users will be charged on an hourly basis, another indicates that applications or users will be charged on a data transfer basis in terms of bytes, and another indicates that the applications or users will be charged a single amount for unlimited use. The billing engine 620 also indicates, not only how applications and users are charged, but also how they billed (e.g., periodically, directly to users, to an organization, etc.). The billing engine 620 may also indicate how medical bills are calculated, compiled, and determined for users of the medical provider services and include the procedures for accessing one's bill. For example, the billing engine 620 may enforce billing structures rules for certain services provided by medical care professionals at medical care facilities. The billing engine 620 may also define the rule under which users (e.g., users, doctors, nurses, etc.) may access their own bills and bills associated with others. In some examples, this may include stripping away certain protected-health information, identifying information, and the like. The engines of the access management engine 602 are accessed via the interface layer 316 discussed later.

Within the audit/compliance layer 312 is located an access log engine 622. The access log engine 622 evaluates the rules and conditions for logging access to the medical provider network by users, applications, devices, and the like. Logging access includes, in some examples, logging data conventionally collected by access log engines running in similar environments. Access log engine 622 can use this data to generate and transmit reports, for example, to stakeholders of the medical provider network such that they can make informed decisions regarding that is accessing the medical provider network and for what purposes.

Within the agency layer 314 is located an agency engine 624. The agency engine 624 evaluates the rules and conditions under which agencies can access the medical provider network. For example, agencies that may use the agency engine 624 include agencies to which the medical provider network provides compliance, tracking, or other reporting information. For example, the agency engine 624 may be used to track one or more performance indicators identified by a government agency, to report occurrences of infectious diseases, and to provide other similar reporting. Thus, in some examples, a government agency uses the agency engine 624 to collect data pertaining to compliance of the medical provider network with one or more statutes or regulations. In some examples, a university is an agency that uses the agency engine 624 to collect data pertaining to one or more studies. In some examples, the agency engine 624 can identify one or more entities (e.g., governmental agencies) that are to receive reports pertaining to medical operations or events and what types of data are to be reported to those entities. The agency engine 624 can then collect the pertinent data, potentially format and/or analyze the data, and facilitate transmission of (e.g., raw, formatted and/or analysis of) the data to the appropriate agency.

Figure 7:
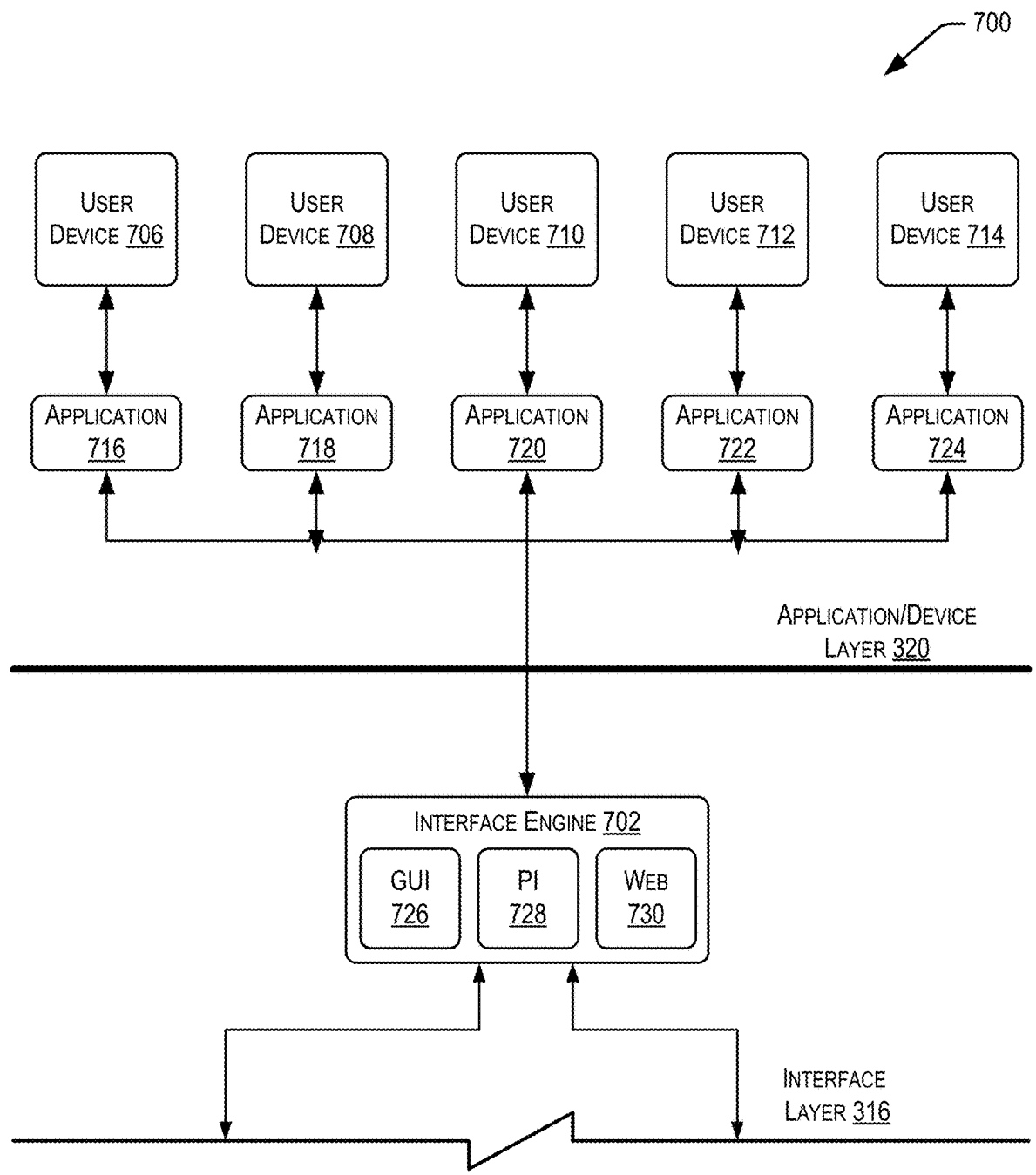
FIG. 7 is an example schematic model illustrating an aspect of the network communication model of FIG. 3 in more detail.

FIG. 7 shows a diagram 700 which depicts a portion of the medical architecture stack 300 according to an embodiment of the invention. In particular, the diagram 700 includes the interface layer 316, and the application/device layer 320. Within the interface layer 316 is located interface engine 702 (e.g., the interface engine 224). The interface engine 702 is configured to generate one or more interfaces (e.g., graphical user interface 726, programmatic interface 728, and/or web interface 730) to enable medical-related data to flow to user devices 710, 712, and 714 via respective applications 720, 722, and 724. In some examples, the interfaces of the interface engine 702 are embodied in hardware, software, or some combination of both. Within the interface layer 316 communications and inputs directed to interacting with elements of the access management layer 310 may be embodied.

The graphical user interface 726 is any suitable graphical user interface configured to interact with elements of the medical provider network. The programmatic interface 728 includes an application programming interface, a programmatic user interface, and other similar interfaces for defining core functions for accessing elements of the medical provider network. For example, the programmatic interface 728 may specify software components in terms of their operations. The web interface 730 is any suitable web interface configured to interact with elements of the medical provider network. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, medical devices capable of capturing inputs, and the like) operated by one or more users of the user devices 706-714. Output may be provided via one or more output devices (e.g., a display or speaker).

The interface engine 702 is utilized by applications internal to the medical provider network and external to the medical provider network to access medical-related data. In some examples, the applications that are internal include applications that are developed for internal use by employees, users, nurses, medical care professionals, medical care providers, contractors, and others associated with the medical provider network. In some examples, the applications that are external to the medical provider network include applications that are developed for external use by those that are not associated with the medical provider network.

Generally, within the application/device layer 320, the applications 716-724 which communicate with other elements of the medical architecture stack 300 using the interfaces generated by the interface engine 702 are defined. This includes detailing how the applications 716-724 are to interact with the interfaces generated by the interface engine 702 for accessing medical-related data. For example, interacting may include accepting inputs at the user devices 706-714 to access medical-related data and, in response, providing the data, prompts, or other types of interaction with one or more users of the user devices 716-714. Thus the applications 716-724 may be related to one or more of the interfaces generated by the interface engine 702. For example, the application 720 may be interact with a graphical user interface (whether generated by the interface engine 702 or otherwise) to interact with other elements of the medical provider network. Interacting may include receiving inputs at the graphical user interface via the application 720, providing output data (e.g., medical-related data including reports, data sets, user record information, diagnosis information, treatment care information, and the like) to the graphical user interface via the application 720, enabling interaction with other user devices, other applications, and other elements of the medical provider network, and the like. For example, some of the inputs may pertain to aggregation of medical-related data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of the applications 720, 722, and 724. In some examples, the applications 720, 722, and 724 include a variety of different applications that can be designed for particular users and/or uses. In one example, the application 720 is specific for doctors. In this example, the application 720 includes dashboards, widgets, windows, icons, and the like that are customized to the individual doctor. In some examples, the application 720 may present different medical-related data depending on a specialty associated with the doctor and protected health information associated with the doctor's user. In this manner, the application 720 adapts and automatically adjusts depending on the context in which the doctor is using the application. In some examples, the medical-related data indicates performance statistics for the doctor, metrics relating to where the doctor falls along a distribution of other similar doctors, outlier users, trends in diagnosis numbers and release, rapid changes in health-related values for the doctor's users compared to other similar users, and the like. The application 720 may be configured to receive input, adjust presentations, present unprompted alerts, adjust display of content, move more relevant content to the foreground, move less relevant content to the background, populate forms for the doctor to order tests, and the like.

In another example, the application 722 may be specific for nurses or types of nurses. In this example, the application 722 may include dashboards, widgets, windows, icons, and the like that are customized to individual nurses. Similar to the example discussed above pertaining to the doctor, in some examples, the application 724 may present different medical-related data depending on a position of the nurse. In this manner, the application 722 adapts and automatically adjusts depending on the context in which the nurse is using the application. For example, the nurse may receive medical-related data, such as test results for a user.

In some examples, the application 724 may be a multi-role application for administrators and is used to manage users and others that constitute the population of the entities or organizations within the medical provider network. Similar to the other examples discussed, in some examples, the application 724 may present different medical-related data depending on a role of the user who is using the application 724. In this manner, the application 724 adapts and automatically adjusts depending on characteristics of the user who is using the application 724. In this manner, the application 724 provide different medical-related data depending on the role of the user. For example, to an administrator may be presented identifying or de-identified information that characterizes overall flow of users within a hospital (e.g., intake date, insurance, bed location, expected checkout date, etc.).

In some examples, the application 724 may be a business intelligence application. In this example, the application 724 is used to display business information generated by components of the medical provider network. This business information can be used for operations, planning, and forecasting. Such business information may include medical-related data because such data may impact operations, planning, forecasting, and the like. Accordingly, the application 724 may present de-identified information in the form of one or more metrics, indicators, or the like as they pertain to business intelligence.

The applications 716 and 718 shown in connection with the interface engine 702 are applications developed by third-parties. In some examples, such applications include any suitable application that benefits from accessing medical-related data. For example, the application 716 may be a health application, a nutrition application, a fitness application, and other similar applications. The medical provider network may include medical-related data pertaining to hundreds of thousands of users. Having data pertaining to so many users presents security concerns. For example, much of the medical-related data may be identifying data. Certain disclosure laws may prohibit the disclosure of such information. Accordingly, data that may be accessed by the applications 716 and 718 may be limited. In some examples, a user of the medical provider network may use one of the applications 716, 718 to access his or her own medical-related data. In this example, the identity of the user may be verified in accordance with techniques described herein.

The user devices 706-714 are any suitable user devices capable of running the applications 716-724. The user devices 706-714 are examples of the user device 228. In some examples, the user devices include: mobile phones, tablet computers, laptop computers, wearable mobile devices, desktop computers, set-top boxes, pagers, and other similar user devices. In some examples, at least some of the user devices 706-714 are the same devices as at least some of the one or more components 410-418. In some examples, the user devices 706-714 may include complementary layers to the application/device layer 320 and/or the receiving layer 302. For example, the user devices 706-714 may include a transmission layer, a generation layer, and/or a receiving layer to communicate data at the application/device layer 320 and at the receiving layer 302.

Figure 8:
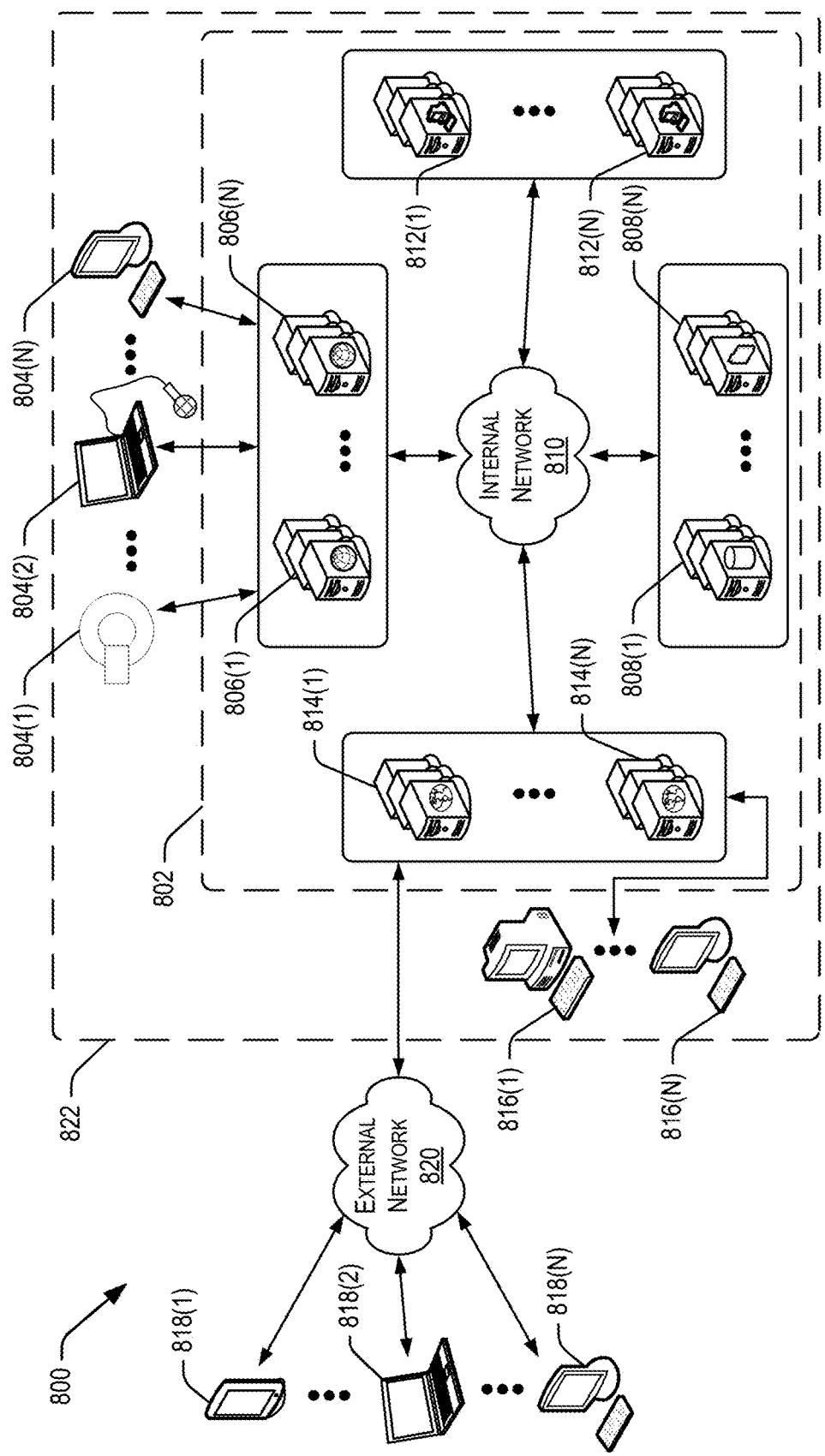
FIG. 8 is an example schematic architecture illustrating a network in which techniques relating to executing reservation of resources for authorized users as described herein may be implemented, according to at least one example.

Turning now to FIG. 8, a medical provider network 800 is shown in accordance with an embodiment of the invention. The medical provider network 800 includes an internal organization 822 including a transformative integration engine 802. The transformative integration engine 802 is an example of the transformative integration engine 202 previously discussed. The medical provider network 800 is illustrated as an example configuration for implementing the techniques described herein. In particular, a configuration of elements as illustrated in FIG. 8, at least in some examples, communicates according to the layers of the medical architecture stack 300. For example, the internal organization 822 includes generation components 804(1), 804(2), and 804(N) which provide medical-related data to aggregation servers 806(1)-806(N).

The generation components 804(1), 804(2), and 804(N) operate in accordance with the receiving layer 302. In some examples, the generation component 804(1) is an MRI machine, a type of medical equipment, the generation component 804(2) is computer with a data collection device, a type of lab system, and the generation component 804(N) is a terminal, which is a type of business component or clinical component. The aggregation servers 806(1)-806(N) operate in accordance with the aggregation layer 304. The aggregation servers 806(1)-806(N) share medical-related data with data storage servers 808(1)-808(N) via one or more internal network(s) 810. In some examples, the internal network 810 is any suitable network capable of handling transmission of medical-related data. For example, the internal network 810 may be any suitable combination of wired or wireless networks. In some examples, the internal network 810 may include one or more secure networks. The data storage servers 808(1)-808(N) are configured to store medical-related data in accordance with the active unified data layer 308. The data storage servers 808(1)-808(N) include database servers, file storage servers, and other similar data storage servers.

Access management servers 812(1)-812(N) manage access to the medical-related data retained in the data storage servers 808(1)-808(N). The access management servers 812(1)-812(N) communicate with the other elements of the medical provider network 800 via the internal network 810 and in accordance with the access management layer 310.

Interface servers 814(1)-814(N) provide one or more interfaces applications to interact with the other elements of the medical provider network 800. The interface servers 814(1)-814(N) provide the one or more interfaces and communicate with the other elements of the medical provider network 800 via the internal network 810 and in accordance with the interface layer 316. The interfaces generated by the interface servers 814(1)-814(N) can be used by internal user devices 816(1)-816(N) and external user devices 818(1), 818(2), and 818(N) to interact with elements of the medical provider network 800.

The internal user devices 816(1)-816(N) are examples of the user devices 706-714. In some examples, the internal user devices 816(1)-816(N) run applications for patients, doctors, specialists, nurses, administrative professionals, network administrators, business leaders, and others that access the other elements of the medical provider network 800 via the interfaces generated by the interface servers 814(1)-814(N). As an additional example, the external user devices 818(1), 818(2), and 818(N) run applications developed by third parties for patients, doctors, specialists, nurses, administrative professionals, network administrators, business leaders, and others that access the other elements of the medical provider network 800 via the interfaces generated by the interface servers 814(1)-814(N).

The external user devices 818(1), 818(2), and 818(N) access the interfaces via external network 820. In some examples, the external network 820 is an unsecured network such as the Internet. The external user devices 818(1), 818(2), and 818(N) are examples of the user devices 706-714. The external user device 818(1) is a mobile device. In some examples, the mobile device may be configured to run an application to access the medical provider network 800. Similarly, the other external user devices 818(2)-818(N) run applications that enable them to access the medical provider network 800. While the medical provider network 800 is shown as implemented using discrete servers, it is understood that it may be implemented using virtual computing resources and/or in a web-based environment.

Figure 9:
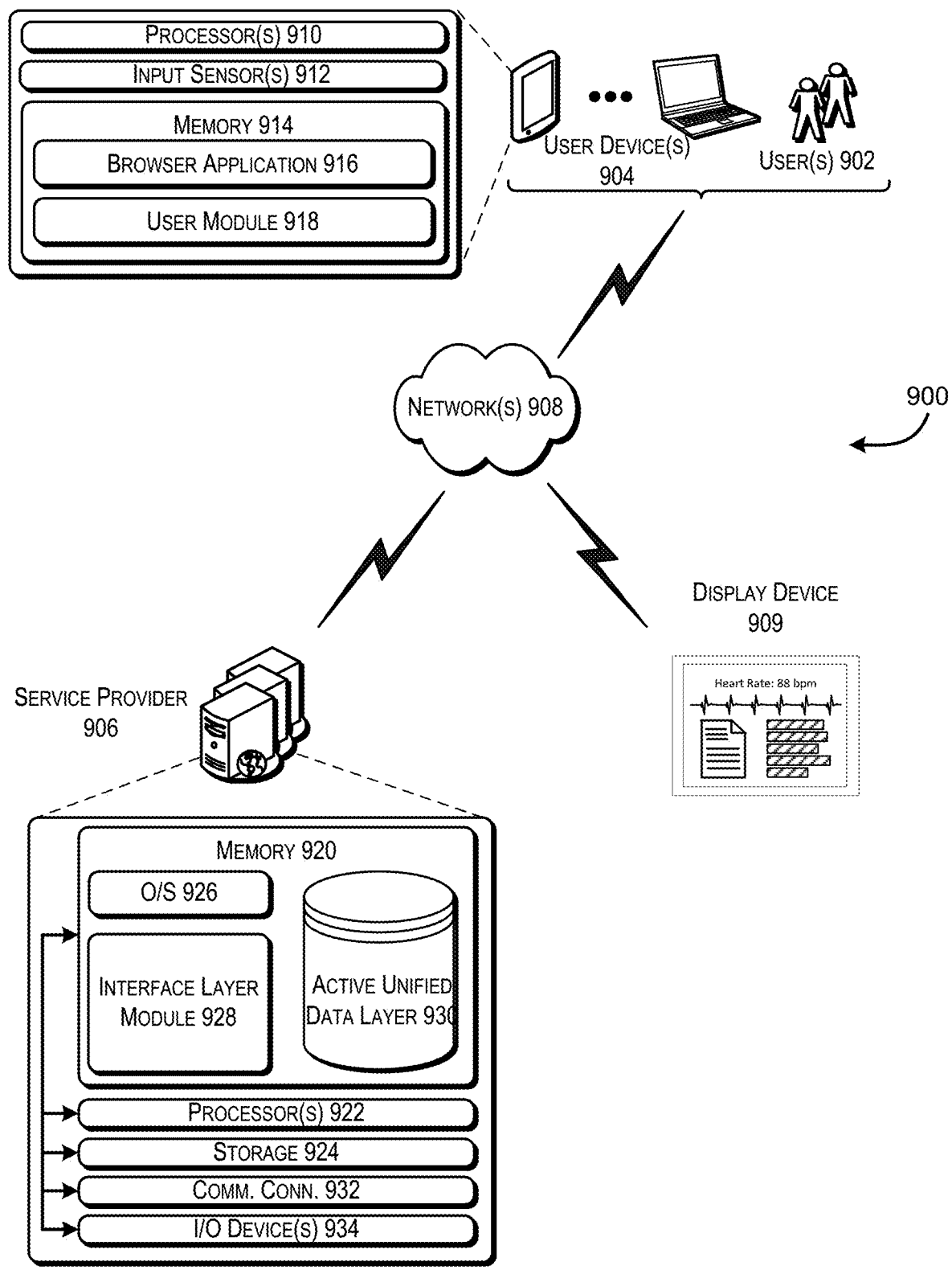
FIG. 9 depicts aspects of an example system or architecture in which a customizable electronic display device may be implemented.

FIG. 9 depicts aspects of an example system or architecture 900 in which a customizable electronic display device may be implemented. In architecture 900, one or more users 902 may utilize user devices 904. In some examples, the user devices 904 may be in communication with a service provider 906 via the network(s) 908, or via other network connections. In some examples, the user devices 904 and/or the service provider 906 may be in communication with a display device 1009 via the network(s) 908, or via other network connections.

The user devices 904 may be any type of computing device such as, but not limited to, a mobile phone, a smart phone, a personal digital assistant (PDA), a laptop computer, a desktop computer, a server computer, a thin-client device, a tablet PC, etc. Additionally, user devices 904 may include a wearable technology device, such as a watch, wristband, earpiece, a pair of glasses, or any other suitable wearable technology. In addition, the user device may include location tracking technology, such as a real time location system (RTLS) tag. The user device 904 may include one or more processors 910 capable of processing user input. The user device 904 may also include one or more input sensors 912 for receiving user input. As is known in the art, there are a variety of input sensors 912 capable of detecting user input, such as accelerometers, cameras, microphones, or any other suitable sensor device. The user input obtained by the input sensors may be from a variety of data input types, including, but not limited to, audio data, visual data, or biometric data. Embodiments of the application on the user device 904 may be stored and executed from its memory 914.

Turning to the contents of the memory 914 in more detail, the memory 914 may include a browser application 916. The memory 914 may also include a user interface module 918 that is capable of issuing commands to the service provider 906 and/or the display device 1009. Although sample architecture 900 depicts a user interface module 918 as being included in the contents of the memory 914 of the user device 904, some embodiments may not include a user interface module 918 in memory 914 of the user device 904. In those embodiments in which the user interface module 918 is not included in memory 914, input received by the input sensors 912 may instead be processed by the service provider 906. This will be described in detail below.

In accordance with at least one embodiment, the user interface module 918 may be configured to communicate commands to the service provider 906 and/or the display device 1009. In accordance with at least one embodiment, the user interface module 918 may include a graphical user interface (GUI) that allows the user(s) 902 to configure the information displayed by display device 1009. For example, from user device 904, a user may be able to set user preferences or set up rules to determine what information is presented or how it is presented. In accordance with at least one embodiment, the user interface module 918 may be a downloadable software application.

In some examples, the network(s) 908 may include any one or a combination of many different types of networks, such as cable networks, the Internet, wireless networks, cellular networks, and other private and/or public networks. While the illustrated example represents the users 902 accessing the service provider 906 over the network(s) 908, the described techniques may equally apply in instances where the users 902 interact with a service provider 906 via the user device 904 over a landline phone, via a kiosk, or in any other manner. It is also noted that the described techniques may apply in other client/server arrangements (e.g., set-top boxes, etc.), as well as in non-client/server arrangements (e.g., locally stored applications, peer to-peer systems, etc.).

As described briefly above, the browser application 916 may allow the users 902 to interact with a service provider 906, such as to store, access, and/or manage data, develop and/or deploy computer applications, and/or host web content. The one or more service provider(s) 906, perhaps arranged in a cluster of servers or as a server farm, may host the browser application 916. These servers may be configured to host a website (or combination of websites) viewable via the user device 904 or a web browser accessible by a user 902. Other server architectures may also be used to host the browser application 916. The browser application 916 may be capable of handling requests from many users 902 and serving, in response, various user interfaces that can be rendered at the user device 904 such as, but not limited to, a web site. The browser application 916 can be any type of website that supports user interaction, including social networking sites, electronic retailers, informational sites, blog sites, search engine sites, news and entertainment sites, and so forth. As discussed above, the described techniques can similarly be implemented outside of the browser application 916, such as with other applications running on the user device 904.

The service provider 906 may be any type of computing device such as a mobile phone, a smart phone, a personal digital assistant (PDA), a laptop computer, a desktop computer, a server computer, a tablet PC, or any other suitable computing device. Additionally, it should be noted that, in some embodiments, the service provider 906 may be executed by one more virtual machines implemented in a hosted computing environment. The hosted computing environment may include one or more rapidly provisioned and released computing resources, which computing resources may include computing, networking, and/or storage devices. A hosted computing environment may also be referred to as a cloud-computing environment.

In one illustrative configuration, the service provider 906 may include at least one memory 920 and one or more processing units (or processor(s)) 922. The processor(s) 922 may be implemented as appropriate in hardware, computer-executable instructions, firmware or combinations thereof. Computer-executable instruction or firmware implementations of the processor(s) 922 may include computer-executable or machine-executable instructions written in any suitable programming language to perform the various functions described.

The memory 920 may store program instructions that are loadable and executable on the processor(s) 922, as well as data generated during the execution of these programs. Depending on the configuration and type of service provider 906, the memory 920 may be volatile (such as random access memory (RAM)) and/or non-volatile (such as read-only memory (ROM), flash memory, etc.). The service provider 906 may also include additional storage 924, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 920 may include multiple different types of memory, such as static random access memory (SRAM), dynamic random access memory (DRAM) or ROM. Turning to the contents of the memory 920 in more detail, the memory 920 may include an operating system 926 and one or more application programs or services for implementing the features disclosed herein including at least a module for filtering and displaying information to a user (interface layer module 928). The memory 920 may also include an active unified data layer 930, which contains aggregated medical-related data. The active unified data layer 930 is an example embodiment of the active unified data layer 308 of FIG. 3. In accordance with at least one embodiment, the active unified data layer 930 may consist of data stored in a database.

The memory 920 and the additional storage 924, both removable and non-removable, are examples of computer-readable storage media. For example, computer-readable storage media may include volatile or non-volatile, removable or non-removable media implemented in any method or technology for storage of information such as computer-readable instructions, data structures, program modules or other data. As used herein, modules may refer to programming modules executed by computing systems (e.g., processors) that are part of the user device 904 or the service provider 906. The service provider 906 may also contain communications connection(s) 932 that allow the service provider 906 to communicate with a stored database, another computing device or server, user terminals, and/or other devices on the network(s) 908. The service provider 906 may also include input/output (I/O) device(s) and/or ports 934, such as for enabling connection with a keyboard, a mouse, a pen, a voice input device, a touch input device, a display, speakers, a printer, etc.

Turning to the contents of the memory 920 in more detail, the memory 920 may include an operating system 926, a database containing active unified data layer 930 and the one or more application programs or services for implementing the features disclosed herein, including an interface layer module 928.

In accordance with at least one embodiment, the interface layer module 928 may be configured to receive data from the user interface module 918 and filter/select data from a common database maintained by active unified data layer 930 to be displayed to a user. In accordance with at least one embodiment, data may be filtered/selected for presentation based on predetermined constraints. In accordance with at least one embodiment, the service provider 906 may display data in response to receiving input data from input sensor(s) 912 on user device 904. In accordance with at least one embodiment, data may be selected for presentation based on received object (any asset, including a person) location data (e.g., real time location system data). For example, information related to an object may be displayed or removed from display upon determining that the object has entered or exited the vicinity of the display device 1009. In accordance with at least one embodiment, data may be selected for presentation based on received commands or gesture input. This is described in more detail with relation to FIG. 11 below. In accordance with at least one embodiment, data that is filtered and/or selected for presentation may be customized to account for user and/or presenter needs. This is described in more detail with regard to FIG. 10 and FIG. 11 below.

Data stored in the active unified data layer 930 common database may be predetermined or it may be dynamically generated. For example, medical-related data in the active unified data layer 930 may be updated at particular intervals or in real-time. Furthermore, data being updated data in the active unified data layer 930 may be queried from data sources in parallel or sequentially. In accordance with at least one embodiment, the active unified data layer 930 may contain medical-related data, which may include any user metadata or treatment-related documents (e.g., x-ray images, ultrasound images). Data stored by active unified data layer 930 may be encrypted. The active unified data layer 930 may also maintain a set of decryption keys for data in the common database.

The display device 1009 may be any device capable of presenting information to at least one person. In accordance with at least one embodiment, the display device 1009 may be a thin client device. In accordance with at least one embodiment, the display device 1009 may also be a user device 904 as depicted in FIG. 9. Display device 1009 may be equipped with any number of input sensors capable of detecting user input, such as cameras, microphones, a keyboard (including an GUI keypad) or any other suitable sensor device. The user input obtained by the input sensors may be from a variety of data input types, including, but not limited to, audio data, visual data, and biometric data. For example, the display device 1009 may be equipped with cameras capable of utilizing facial recognition techniques. In accordance with at least one embodiment, the display device 1009 may be equipped with eye-tracking cameras capable of detecting a user's focus. Although the data selection and filtering is depicted as being performed by interface layer module 928 on service provider 906, it is envisioned that at least a portion of the data selection and filtering may be performed on display device 1009.

Figure 10:
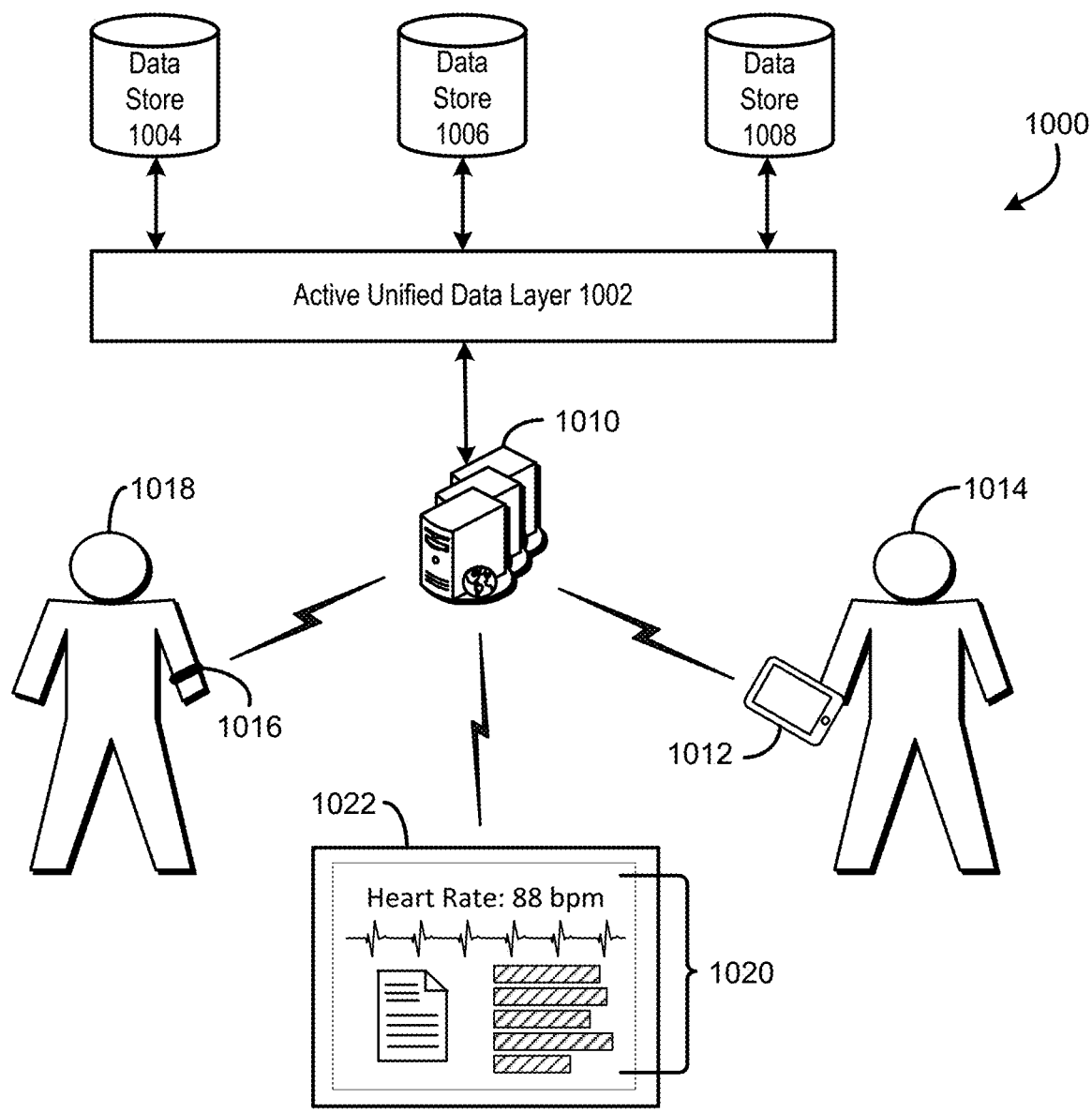
FIG. 10 shows a diagram that depicts an example of a data communication flow and presentation in accordance with at least one embodiment of the disclosure.

FIG. 10 shows a diagram 1000 that depicts an example of a data communication flow and presentation in accordance with at least one embodiment of the disclosure. In FIG. 10, an active unified data layer 1002 is depicted and receiving data from various data stores 1004, 1006, and 1008. Active unified data layer 1002 is an example active unified data layer 308 of FIG. 3. Data stores 1004, 1006, and 1008 are examples of data store 226 of FIG. 2. The active unified data layer 1002 may be aggregated and store data from any number of data stores 1004, 1006 and 1008. Data stored in an active unified data layer may be updated from data stores sequentially or in parallel.

In accordance with at least one embodiment, active unified data layer 1002 may be stored on, or accessible by, a service provider 1010. Service provider 1010 is an example service provider 906 of FIG. 9. In addition to accessing data located in active unified data layer 1002, service provider 906 may receive data from a user device 1012, which is depicted in FIG. 9 as being operated by user 1014. User device 1012 is an example mobile device in accordance with at least on embodiment. User device 1012 may contain a number of sensors via which input data may be received. Through user device 1012, user 1014 may provide data to the service provider 1010 either intentionally or unintentionally. For example, user device 1012 may provide its location data to the service provider 1010 without any interaction from the user 1014. In accordance with at least one embodiment, service provider 906 may also receive data from a wearable device 1016, such as that depicted as being worn by user 1018. Wearable device 1016 may provide service provider 906 with data related to the user 118, such as biometric data (e.g. heart rate), location data, or any other suitable user-related data. User devices 1012 and 1016 are example user device(s) 904 of FIG. 9. In accordance with at least one embodiment, service provider 1010 may also send data to user devices 1012 and 1016. For example, service provider 1010 may send educational material or medical data to user device 1012 for presentation to user 1014. In accordance with at least one embodiment, the service provider 1010 may send information to a user device when it receives an indication that the user device 1012 has met a specified condition (e.g., the user device has entered a particular area or is in the vicinity of a particular asset).

In accordance with at least one embodiment, service provider 1010 may provide medical-related data 1020 to a display device 1022 for presentation. Medical-related data may contain treatment-related documents (e.g., x-ray images, ultrasound images, magnetic resonance imaging images, etc.), biometric data (e.g. heart rate, blood pressure, glucose levels, etc.), user input data (e.g., hospital discharge date, user pain level, health care provider comments, etc.), or any other suitable information relevant to one or more users. As described above, the data chosen for display by the service provider 1010 may be obtained from a number of sources, including, but not limited to, the active unified data layer 1002, various data stores, manual input, and user devices. Although FIG. 10 depicts data from data stores 1004, 1006, and 1008 as being accessed through the active unified data layer 1002, it is envisioned that one or more data stores may be accessed directly by service provider 1010. Furthermore, although FIG. 10 depicts the service provider 1010 as being separate from display device 1022, it is envisioned that the display device 1022 may contain service provider 1010.

In accordance with at least one embodiment, actions or information may be associated with commands and/or gestures. In accordance with at least one embodiment, users may be provided with the ability to customize (e.g., alter, remove, or add) associations between gestures and presentation data to be displayed on display device 1022. For example, a user may be provided with the ability to customize the information presented, the order in which the information is presented, the timing of the presentation, or the presentation style of that information. For example, a particular presenter may wish to present information in a particular order when speaking with users. In this example, the presenter could customize the order and/or style that the information is presented in and each time that the presenter presents this information, the customization will be applied. The presenter may also customize the level of detail that is presented to the user. In addition to formats and presentation styles, this customization may also include specific gesture or voice activation customizations. For example, a presenter may like to use a specific hand gesture in order to highlight a specific section of a document such as an x-ray image or a chart that a user should focus on. Customization of these gestures or commands will be described in greater detail with relation to FIG. 11 below. In accordance with at least one embodiment, information or actions may be associated with voice commands or keywords. For example, a presenter may wish to have the system present a definition or additional educational material when he mentions a specific medical condition or term. Customizations may apply to each presenter in the system or they may be set for one (or a selected group of) presenter(s).

In accordance with at least one embodiment, information presentation may be customized to account for a user context. In accordance with at least one embodiment, data regarding user requirements, such as clinical or demographic requirements, stored by the service provider may be used to filter and/or enhance information presentation. For example, a user's eyesight information may be used to determine the font size in which data is presented to that user. In this example, a hospital user with bad eyesight may be presented with information in a larger font. By way of further example, a user may have a language preference other than English. In this example, information might be presented in another language for that user. In another example, information might be made age-appropriate for a specific user by presenting information that someone of that user's age group may be more interested in. In accordance with at least one embodiment, data may be formatted and/or presented when certain conditions are met. For example, medications may have allergy and/or reaction data that is displayed if the user is allergic to or taking another medication adverse to it. Furthermore, it may be appropriate to customize the data that is not presented. For example, the service provider 1010 might elect not to display specific information for a user who is labeled as a suicide risk. These contextual customizations may be associated with a particular user so that each time information is presented to that user, the customizations are applied to the information being displayed.

Figure 11:
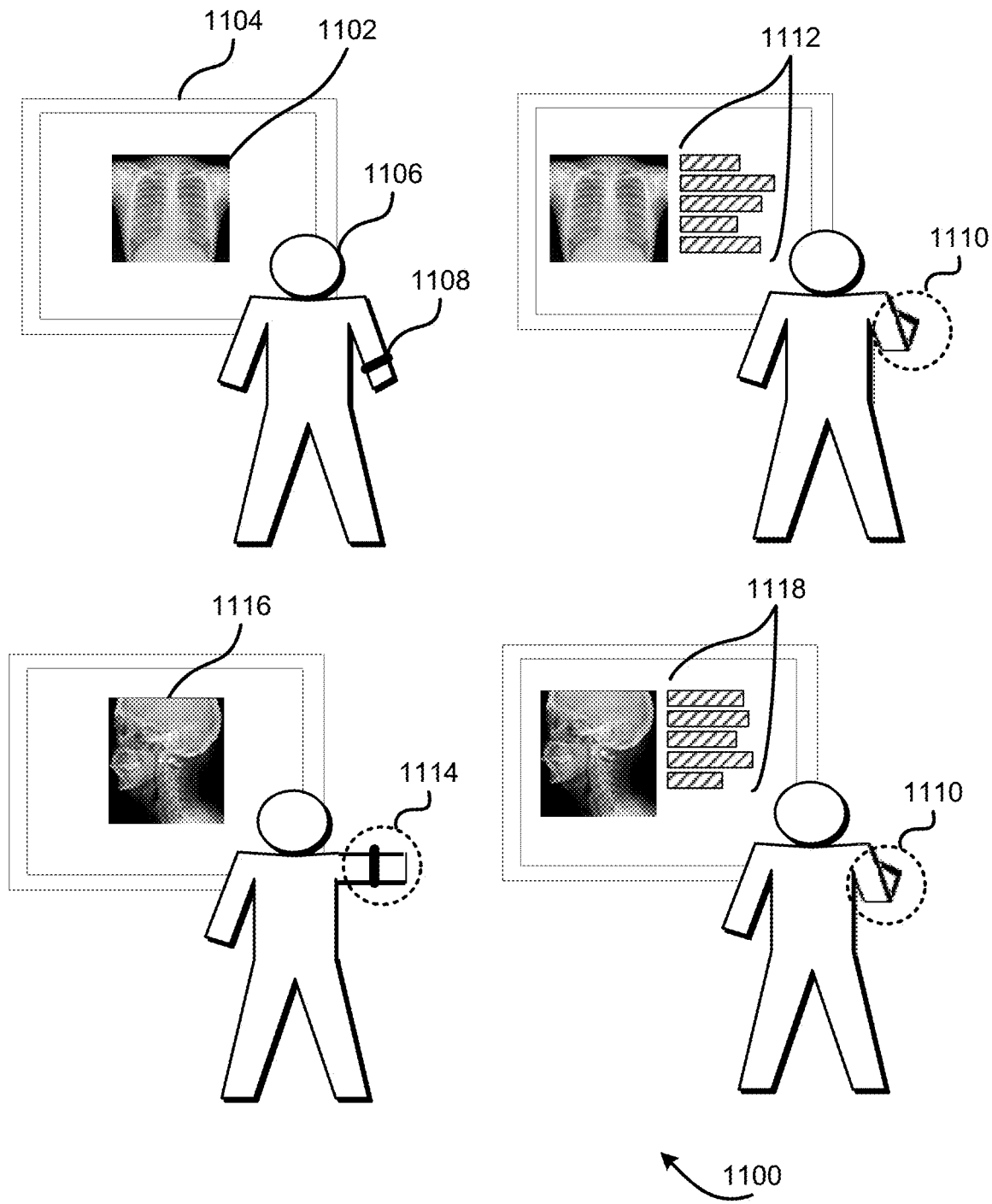
FIG. 11 illustrates an example embodiment of the current disclosure in which a user is capable of interacting with a display device.

FIG. 11 illustrates an example embodiment of the current disclosure in which a user is capable of interacting with a display device. In example embodiment 1100, a first piece of medical information 1102 may be requested and subsequently depicted on a display device 1104. Medical information 1102 may be any information relating to a user. The display device 1104 may be any device capable of presenting information to a user 1106, such as a monitor or a television. A user 1106 may be any person with authorization to view data on the display device. In one example, the user 1106 may be a user or a presenter that wishes to view user-related information on the display device 1104. For example, the user 1106 may be a cafeteria worker who wishes to see a user's dietary restrictions and/or food allergies. In this example, the cafeteria worker may be prevented from viewing any information other than food-related user information.

In accordance with at least one embodiment, a user 1106 may possess a mobile device capable of communicating user input to the display device 1104. In accordance with at least one embodiment, a separate sensor, such as a camera located on the display device 1104, may detect gestures made by the user 1106. The separate sensor may include an eye-tracking camera, a camera capable of facial recognition, an audio sensor, or any other suitable sensor device. For the purposes of this application, a gesture is any action taken by the user 1106 that may be interpreted by the described system. In accordance with at least one embodiment, a user 1106 may possess a wearable device 1108. In these embodiments, the wearable device 1108 may track movements made by the user 1106 or his or her location.

In accordance with at least one embodiment, an application may be used to register one or more performable gestures with an operating system or an operating system service (e.g., an interruption handler or other service configured to receive user input and provide information to the applications in response to the input). In this way, a registry file may be built, updated, or otherwise modified to include a list, set, or other grouping of performable gestures. The registry (also referred to as registration) information may associate certain performable gestures with certain operations and/or actions that the service provider may be configured to execute. When a first gesture 1110 is performed by the user 1106, an action associated with the first gesture 1110 may be executed. For example, the action associated with the first gesture 1110 may be to display secondary content 1112 associated with the first piece of medical information 1102, such as a more in-depth analysis, doctors' notes, or any other suitable information.

In accordance with at least one embodiment, a second gesture 1114 may be performed by the user 1106. The second gesture 1114 may be associated with one or more additional actions. For example, the second gesture 1114 may cause the display device 1104 to present a second piece of medical information 1116. When viewing the second piece of medical information 1116, the user 1106 may then perform the first gesture 1110 again in order to display secondary content 1118 associated with the second piece of medical information 1116. Although FIG. 11 depicts two gestures or commands, it is envisioned that any number of gestures may be associated with actions or information.

For an illustration of example implementation 1100, a user 1106 who is reviewing medical information may choose to view a first piece of medical information 1102 on display device 1104. The user 1106 may then perform the first gesture 1110 and have secondary content 1112 presented to him or her. If the user 1106 determines that he/she is done viewing this information, or the user wishes to view another piece of information, then he or she may perform a second gesture 1114 to display information related to a second piece of medical information 1116. The second piece of medical information 1116 may replace the first piece of medical information 1102 or they may be displayed together. The user 1106 may then perform the first gesture 1110 to display secondary content 1118 associated with the second piece of medical information 1116.

For an alternative illustration of example implementation 1100, a user 1106 may be presented with first piece of medical information 1102 on display device 1104. If the user 1106 is determined to be interested in the first piece of medical information 1102 being presented, then the display device 1104 may present secondary content 1112 related to the first piece of medical information 1102 in addition to what was previously presented. Interest in the first piece of medical information 1102 may be determined upon detection of a first gesture 1110, such as if the user 1106 looks at, points to, nods at, or mentions the item depicted by the display device 1104. By way of further illustration, the user 1106 may focus on or spend a long time looking at a particular term or figure that is displayed. In this example, it may be determined that the user 1106 is having difficulty understanding the term or figure. In response to making that determination, a definition or explanation (secondary content 1112) may be presented to the user 1106.

In accordance with at least one embodiment, a user (e.g., a health care provider, a patient, an administrator, etc.) is able to associate a gesture with an action to be taken. For example, a presenter may customize associations between gestures and actions to be taken or information to be displayed. In this example, the presenter may associate a particular medical term with an action to display a definition or educational material related to the term. When the medical term is mentioned by the presenter, that action may be taken and the definition or educational material may be displayed on the display device 1104. In another example, a user may elect to associate a specific hand gesture with an action to highlight text. In this example, a specific hand gesture may be used by the user to highlight a specific section of information or text on the screen of the display device 1104. The ability to customize associations between gestures and actions may be provided to a user by an application via a graphical user interface (GUI). Once a user has associated a gesture with an action, the association may be stored in a data store at the service provider. In accordance with at least one embodiment, the gesture selected by the user may be part of a predefined library of gestures. In accordance with at least one embodiment, the application may enable the user to define an entirely new gesture (e.g., a shape or motion that is not already assigned to any action), and then provide an action association for that gesture.

Although FIG. 11 focuses on the use of gestures to facilitate communication between a user 1106 and the display device 1104, it is envisioned that this communication may take the form of any number of suitable communication methods. For example, information 1102 may be presented in response to receiving typed user input, it may be presented at a particular time, it may be automatically presented (e.g. as part of a screen saver), or it may be presented as a user 1106 approaches the display device 1104. By way of further example, in embodiments in which RTLS or a similar technology is being utilized, information related to a presenter may be displayed as the presenter enters the room in which the display device is located. In this example, the presenter's picture may be presented along with the presenter's name, position, expertise, years of experience, or any other suitable information.

Figure 12:
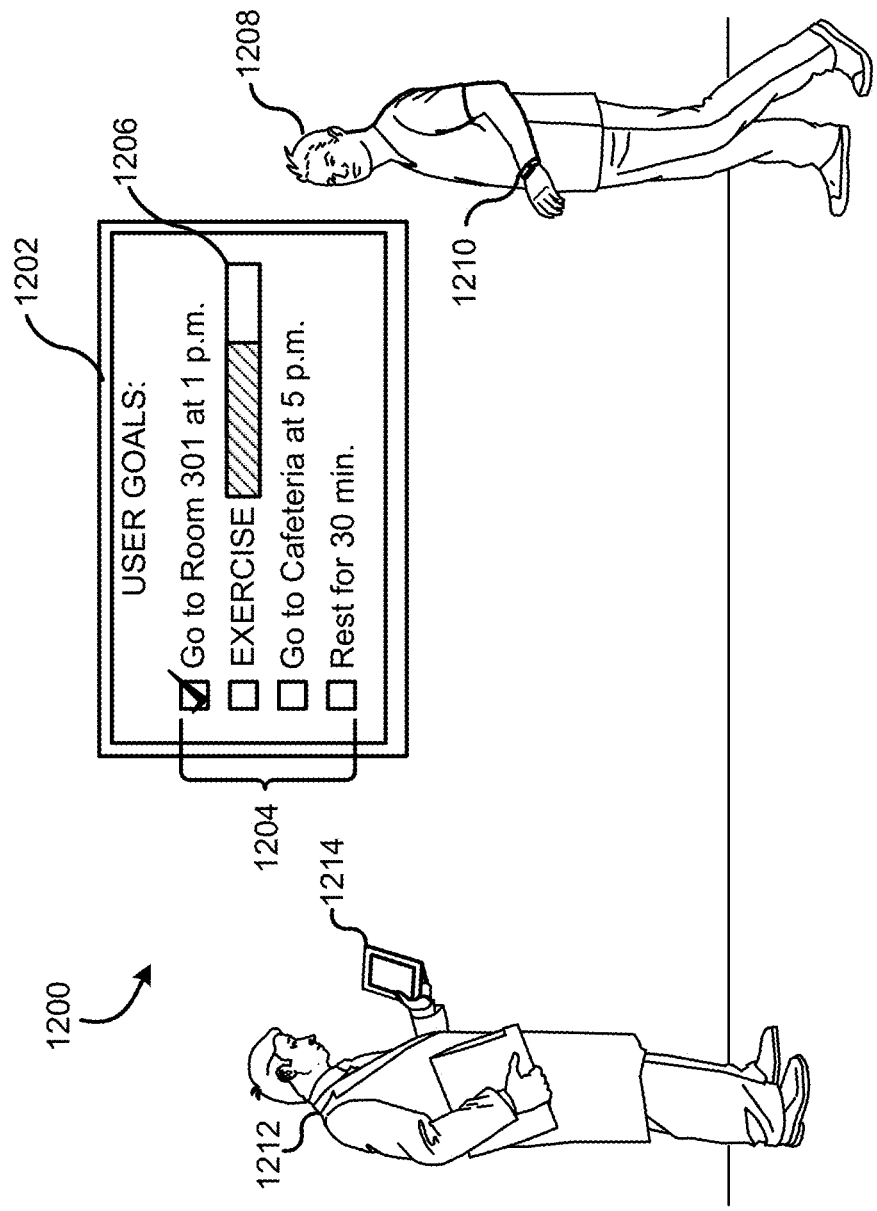
FIG. 12 shows a diagram 1200 which depicts an example of setting and automatic tracking of user goals in accordance with at least one embodiment of the invention.

FIG. 12 shows a diagram 1200 which depicts an example of setting and automatic tracking of user goals in accordance with at least one embodiment of the invention. In example embodiment 1200, a display device 1202 is used to depict one or more user goals 1204. The display device 1202 may also depict a progress indicator 1206 associated with one or more of the user goals 1204. The progress indicator 1206 may be any type of indicator, such as a progress bar, a percentage, a notification of remaining time, or any other suitable notice that indicates that a goal has been at least partially completed.

In accordance with at least one embodiment, user goals 1204 may be stored in a data store and may be associated with a particular user 1208. Data may be stored in a database or a text document (including a markup language document such as XML). For example, the following is one format in which a goal set may be stored in an XML document:

<userx>
  <goals>
    <exercise>
      <duration>30 minutes </duration>
      <heartrate>0.6*220—age </heartrate>
    </exercise>
    <gotolocation>
      <time>17:00</time>
      <location>cafeteria </location>
    </gotolocation>
  </goals>
</userx>

In this example, user x has been assigned the goals of exercising for 30 minutes and going to the cafeteria at 17:00. As depicted in the example, each goal has been assigned at least one parameter. For example, the second goal has the parameters "time" and "location" which have been given values "17:00" and "cafeteria" respectively. Additionally, values stored in parameters may contain equations and/or variables. For example, the parameter "heartrate" that is associated with the goal "exercise" contains a mathematical equation for determining an appropriate target heart rate. In this equation, the variable age may be determined at any time from a profile that is associated with the user 1208 (user x in this example) so that the parameter may be calculated dynamically. Although this example depicts user goals 1204 in markup language, a user may be able to input/set them in a different format using a graphical user interface.

In accordance with at least one embodiment, the user 1208 may be equipped with a wearable device 1210 which is capable of detecting location and/or biometric data for the user 1208. The wearable device may be associated with, or checked out to, the user 1208 who is wearing it. Input data that is collected by wearable device 1210 may be sent to a service provider (such as that depicted as 906 in FIG. 9) for processing. Once input data is collected from wearable device 1210, it may be used to determine progress made in each of the goals.

In accordance with at least one embodiment, parameters for user goals 1206 may be based on biometric data. For example, a goal to "exercise" may be associated with keeping an elevated heart rate for a given time. In this example, the wearable device 1210 may provide heart rate data to the service provider, which will determine when the goal has been met. Alternatively, a goal to exercise may be associated with the parameter of burning a given number of calories. In this example, the wearable device 1210 may collect data related to exertion, such as heart rate, the type of exercise being done, or the distance traveled by the user. By way of further example, a goal to "rest" may be associated with the parameter of maintaining a resting heart rate. In accordance with at least one embodiment, parameters for user goals 1206 may be based on location data. For example, a user 1208 may be needed in a particular location at a given time. In this example, the user may be given the goal to go to that location at that time. By way of further example, the user may be asked to walk a particular distance, along a particular path, or to keep moving for a particular amount of time.

Some embodiments of the current disclosure will not require a wearable device 1210. As described earlier in this disclosure, the display device 1202 may be equipped with any number of input sensors. It is envisioned that input from these sensors may also be collected to determine goal completion. For example if a user is given a goal to read a notification, an eye-tracking camera located on or near the display device 1202 may be used to collect eye movement data. In accordance with at least one embodiment, user goals 1206 may be set so that one goal must be completed before any progress is tracked in a subsequent goal.

In accordance with at least one embodiment, user goals 1206 may be generic or set for a group of users. For example, if a hospital serves meals between 5 and 7 p.m., a goal may be set for all users to go to the cafeteria between those times. Alternatively, the hospital may wish to stagger the flow of users to the cafeteria by setting different meal times for various users.

In accordance with at least one embodiment, user goals 1204 may be set by the user 1208 or by a presenter 1212. User goals 1204 may be set via the display device 1202 or via a mobile device 1214 in communication with the display device 1202. User goals 1204 may be input via a graphical user interface located on either device. Once set, user goals 1204 may be associated with the particular user 1208. Additionally, generic or goals for a group of users may be set by a presenter 1212 or an administrator.

For a more specific example of embodiment 1200, a presenter 1212 may, based on his analysis of the user's condition, provide a list of goals for the user 1208. These goals may be aggregated with appropriate generic and/or group user goals as well as any goals set by the user 1208. When a user 1208 approaches a display device 1202, a camera may capture his or her image. The user 1208 may be identified via facial recognition algorithms, location data collected from wearable device 1210, or he or she may be logged in via an alternative method. In this example, once the user 1208 is identified, the user goals 1204 may be displayed along with any appropriate progress indicator 1206. As the user 1208 works toward completion of the user goals 1204, any progress indicators 1206 will continue to update. When the user 1208 has met all of the conditions required for fulfillment of a particular goal, the user goal 1204 information will be updated to indicate that the goal has been completed.

FIG. 13 depicts an example of user presentation and restriction in accordance with at least one embodiment of the invention. In example embodiment 1300, a display device 1302 is depicted as being mounted on a wall. As a first user 1304 approaches the display device 1302, he or she may be identified. In accordance with at least one embodiment, the first user 1304 may be identified as being associated with a wearable device 1306 (such as an RTLS bracelet). In accordance with at least one embodiment, the first user 1304 may be identified using facial recognition techniques. Once the first user 1304 is identified, user authorizations may be determined from an account associated with the first user 1304. In response to the first user 1304 approaching the display device 1302, or in response to a request made by the first user 1304, information may be displayed. In this example, a first document 1308 and a second document 1310 have been displayed on the display device 1302.

When a second user 1312 approaches the display device 1302, he or she may also be identified, and user authorizations may be determined from an account associated with the second user 1312. In accordance with at least one embodiment, the second user 1304 may be identified as being associated with a second wearable device 1314. In accordance with at least one embodiment, the second user 1312 may not be identifiable (e.g., the user is not wearing a bracelet or is not in the database). In that embodiment, the user authorizations for the second user 1312 may be defaulted to non-sensitive information only. In response to the second user 1312 approaching the display device 1302, information may be displayed or removed from display based on user information. In this example, the second document 1310 has been removed from display. Additionally, new information 1316 has been presented. In this example, both the first user 1304 and the second user 1312 must have authorization to view either first document 1308 or information 1316 in order for it to be displayed.

In accordance with at least one embodiment, the information displayed on the display device 1302 may be presenter details (e.g., name, area of expertise, years of practice, etc.) that are automatically displayed when the presenter enters a room. For example, if a user is currently in a room and a presenter is detected as entering the room, the presenter's name and specialty may be displayed on the display device 1302. In accordance with at least one embodiment, the information displayed on the display device 1302 may be related to a user goal as described in FIG. 12. For example, if the second user 1312 has a goal to go to radiology, then information 1316 may be presented in response to the second user 1312 approaching the display device 1302 and may include directions to radiology.

Figure 14:
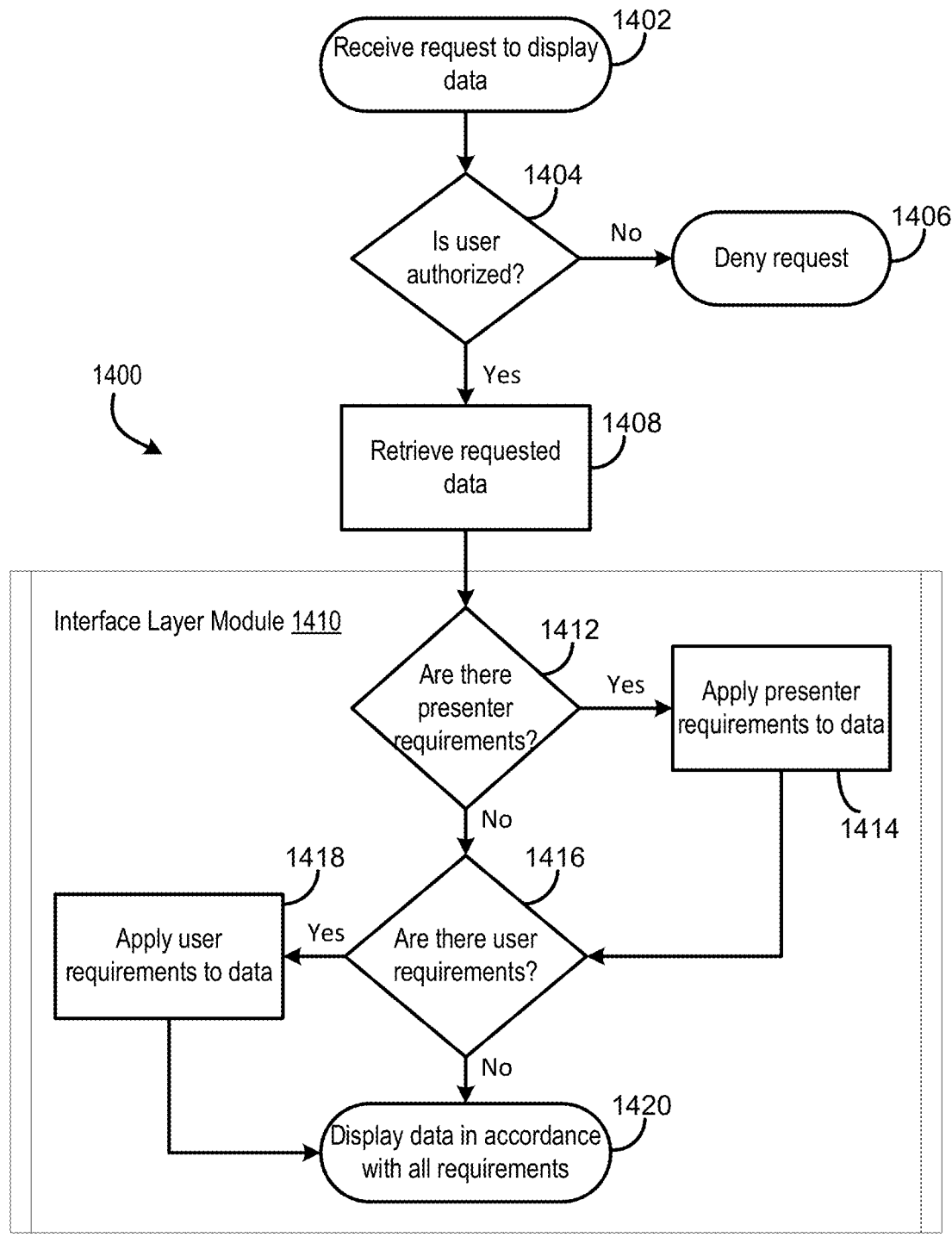
FIG. 14 illustrates an example flow chart showing process 1400 for providing customized presentation of information to a user by a presenter, according to at least a few examples.

FIG. 14 illustrates an example flow chart showing process 1400 for providing customized presentation of information to a user by a presenter, according to at least a few examples. Some or all of the process 1400 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof such as by the system illustrated (user devices 904, service providers 906 and display device 1009) in FIG. 9. The code may be stored on a computer-readable storage medium, for example, in the form of a computer program comprising a plurality of instructions executable by one or more processors. The computer-readable storage medium may be non-transitory.

The process 1400 may begin by receiving a request to present information at 1402. This request may be generated by a user or internally. For example, when a user's location information is received by the system, the system may determine that a particular piece of information should be presented to the user and generate a request without user interaction. Alternatively, a request to present information may be received from a user who wishes to view the information or present it to a second user. Requests may be submitted using gestures, such as voice commands, or via a graphical user interface. Furthermore, the request may be received via a display device or it may be received via a separate mobile device.

At 1404, user authorizations may be checked and access control mechanisms may be enforced. In accordance with at least one embodiment, information may be accessed on the display device as long as an authorized user is present. In this example, the system may receive location information that indicates that an authorized person is or is not present. If no authorized person is present, then the request to display information may be denied at 1406. In accordance with at least one embodiment, access to information may be prevented when an unauthorized person is present. For example, if an authorized person requests access to sensitive information, the request may be denied if it is determined that an unauthorized person is also present. In accordance with at least one embodiment, an override may be made available so that the information may still be viewed as long as certain conditions are met. For example, even if an unauthorized party is present when sensitive information is requested, a presenter may override the access controls and allow its presentation.

At 1408, the relevant data is identified from the request and retrieved from the database. In accordance with at least one embodiment, relevant data may be data related to user goals. In accordance with at least one embodiment, the relevant data may be related to a presenter's diagnosis of a medical condition. The request for this information may be generated automatically when the user and the presenter are both in the same room. In accordance with at least one embodiment, particular pieces of information may be associated with certain gestures or voice commands. As described earlier in this disclosure, these associations may be customized.

Once retrieved, the relevant data is formatted by interface layer module 1410 in accordance with user requirements. Interface layer module 1410 is an example interface layer module 928 depicted in FIG. 9. User requirements may be associated with a user account for a user, a staff member, a presenter, or any other person who may wish to request data from process 1400. User requirements may include presentation styles, content requirements, disability related requirements, or any other suitable parameter that may facilitate, or is necessary for, the learning of or communication of presented material. In accordance with at least one embodiment, relevant data may be formatted with regard to both user requirements and presenter requirements. For example, if a presenter is associated with a particular presentation style, and the user has poor eyesight, then the information may be presented in the presenter's presentation style and in larger font.

At 1412, the interface layer module 1410 may identify the presenter of the information. The presenter may be identified based on RTLS data, facial recognition, a user login, or any number of suitable identification means. Once the presenter is identified, presenter requirements (a set of user requirements associated with a presenter) for that presenter may be identified. The presenter requirements may be associated with a particular presenter, a particular role (e.g., surgeon, radiologist, physician, etc.), a health care facility, or any other suitable category. Presenter requirements may also be default or generic requirements. Presenter requirements may contain rules regulating the way that information is to be presented by that presenter, including the order in which the information is presented, the timing of the presentation, the presentation style of that information, or the level of detail that is presented to a user. In addition to formats and presentation styles, presenter requirements may also include specific gesture or voice commands that are associated with an action or a piece of information. Once the presenter requirements associated with a presenter are identified, they are used to format the requested data at 1414.

At 1416, the interface layer module 1410 may identify the user, or the target of the information. Similar to the identification of the presenter, the user may be identified based on RTLS data, facial recognition, a user login, or any number of suitable identification means. Once the user is identified, user requirements (a set of user requirements associated with a user) for that user may be identified and applied at 1418. User requirements may be preferences associated with a user, based on demographic information (e.g., age, religion, sex, language, etc.), based on medical needs (e.g., poor eyesight, color blindness, deaf, etc.), or based on real-time biometric data. For example, information may be presented in calming colors for a user that currently has an increased heart rate. In accordance with at least one embodiment, user requirements may be default rules that are applied when specific conditions are met. For example, a default user rule may state that any person with a language preference other than English will be presented with information in that language. Although this user requirement is not directly associated with any particular user, each user that meets the condition will have the user requirement applied. In this example, the presenter may additionally be provided with a translation, either on the display device, or on a separate mobile device.

Although 1412 and 1414 are depicted as being performed prior to 1416 and 1418, either step may occur in any order. In accordance with at least one embodiment, steps 1412 and 1414 and steps 1416 and 1418 may be performed several times by the interface layer module 1410 before information is provided for presentation. At 1420, the information is provided to a display device in its formatted state for presentation.

Figure 15:
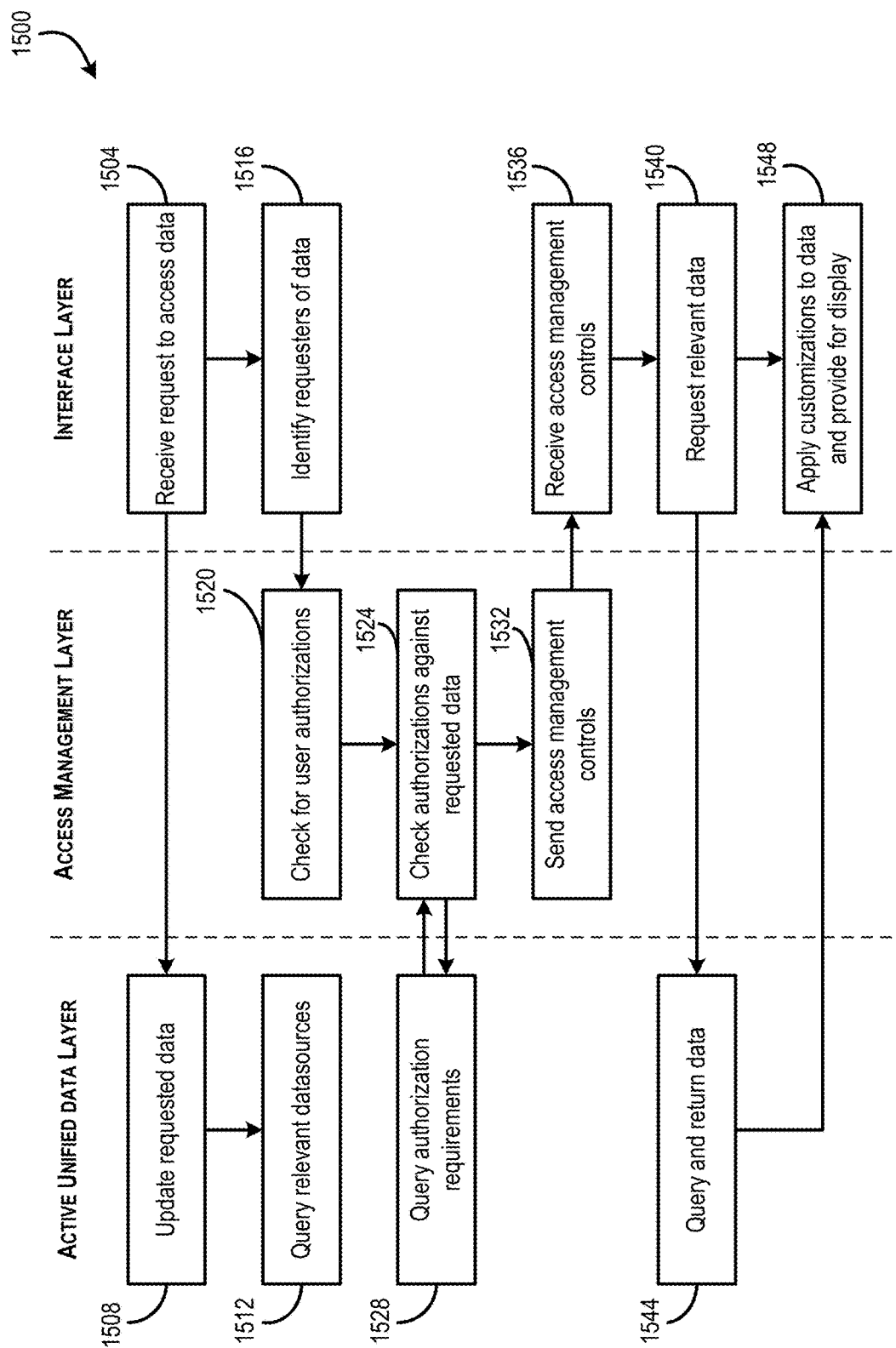
FIG. 15 depicts a swim diagram of another embodiment of process 1500 for updating and providing access to requested content.

FIG. 15 depicts a swim diagram of another embodiment of process 1500 for updating and providing access to requested content. This embodiment details the retrieval and decryption of data for presentation. The depicted portion of process 1500 begins in block 1504 where a request is received by the interface layer. The request may be generated and sent to the interface layer by the application device layer.

In block 1508, the active unified data layer may initiate an update to the requested data in the common database. The update may be initiated in response to receiving an indication that the data has been requested, or it may be updated automatically. For example, updates may be initiated when a determination is made that the current data is out of date or old. Alternatively, data in the active unified data layer's common database may be updated periodically according to an update schedule. To update the information, the active unified data layer may query relevant datasources in parallel or sequentially at block 1512.

In block 1516, the interface layer may identify the requester of the requested data. The requester may be identified based on RTLS data, facial recognition, a user login, or any number of suitable identification means. The requester may be identified based on information (such as login information or device ownership information) sent to the interface layer in the request. In accordance with at least one embodiment, multiple users may be identified as being in the vicinity of a display device. For the purposes of the information request, the interface layer may use access credentials of any user present, such as the user with the highest access level. Once the requester is identified, the interface layer may request access management controls from the access management layer at 1520. Once the request is received at the access management layer, user authorizations may be checked. In accordance with at least one embodiment, the access management layer may maintain a set of user authorizations for each user in the system.

In block 1524, the access management layer may check the user authorizations against authorization required for the requested data. In accordance with at least one embodiment, a level of sensitivity or authorization level may be associated with each piece of data in the common database maintained by the active unified data layer. In these embodiments, the identified user authorizations for the requester may need to match or exceed the authorization level of the data. In these embodiments, authorization requirements may be queried by the active unified data layer at 1528, with the results being returned to the access management layer. In accordance with at least one embodiment, a user may need to be associated with a particular user (e.g., providing treatment for the user) before information related to that user may be accessed.

Each piece of data in the common data store that is maintained by the active unified data layer may be encrypted. In accordance with at least one embodiment, a separate encryption key may be used to encrypt, and a decryption key may be provided for each piece of data. In accordance with at least one embodiment, each level of sensitivity or authorization level of data may share a common encryption and decryption key. Decryption keys may be maintained by the active unified data layer for each piece of data stored in the common database or these decryption keys may be stored by the access management layer. When the authorization requirements are queried by the active unified data layer, it may return a decryption key or an indication of access level required. In accordance with at least one embodiment, the access management layer may determine, based on the received indication, whether the requester should be granted access to the data.

In block 1532, the access management layer may send to the interface layer an indication of whether or not the request is authorized. This indication may be received by the interface layer at 1536. If the request is deemed authorized by the access management layer, the indication may also include one or more decryption keys. In accordance with at least one embodiment, a decryption key will be received by the interface layer for each level of authorization of the requester. For example, upon making a request, a presenter may be provided with all decryption keys to which he or she is granted authorization, and not just the decryption key for the specific data requested. Decryption keys may be stored by the interface layer or the application device layer (on the client device) in temporary memory.

In block 1540, the interface layer may request the data directly from the active unified data layer once the decryption keys have been received. The active unified data layer may query the content and return the encrypted data at 1544. At 1548, the data may be decrypted using one or more of the decryption keys stored in temporary storage and customizations may be applied to the data. The customized data may then be sent to the application device layer to be displayed.

With the decryption key having been sent separately to the interface layer, the active unified data layer may respond to requests in an ambiguous fashion. To clarify, in some embodiments, the active unified data layer may respond to requests without verifying user authorizations or keeping track of requesters of data. Additionally, because the decryption keys have already been obtained, the interface layer would be able to continue to process requests for data without having to reauthorize a particular requester. In accordance with at least one embodiment, decryption keys may be removed from storage when an indication is received that the requester has left the vicinity of the display device. In accordance with at least one embodiment, the displayed information may be removed from the display device upon receiving that indication.

Figure 16:
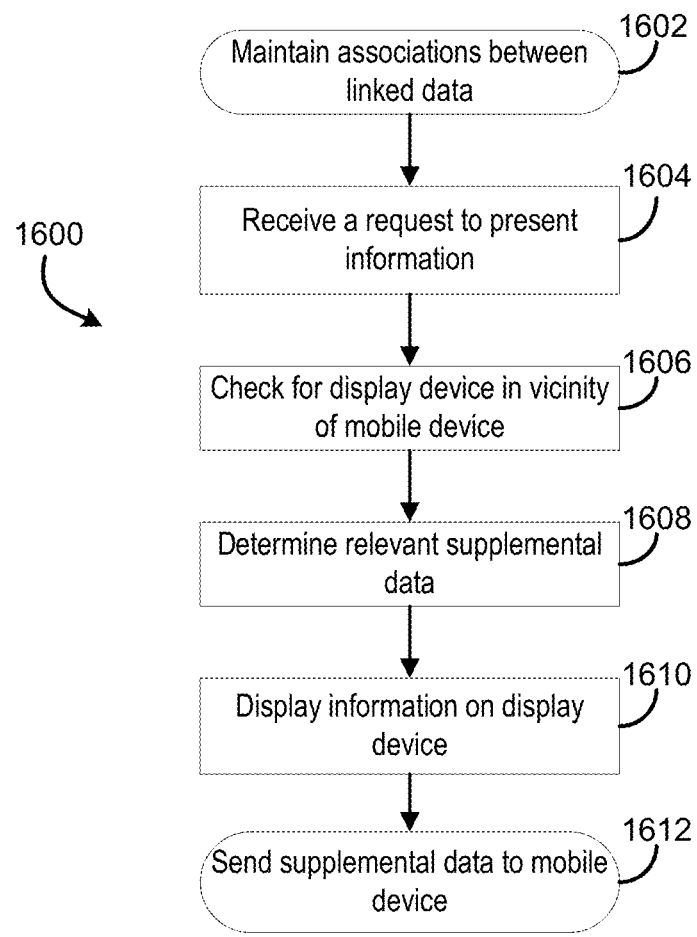
FIG. 16 illustrates an example flow diagram showing process for providing mobile device functionality for presentation of information to a user by a presenter, according to at least a few examples.

FIG. 16 illustrates an example flow diagram showing process 1600 for providing mobile device functionality for presentation of information to a user by a presenter, according to at least a few examples. Some or all of the process 1600 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof such as by the system illustrated (user devices 904, service providers 906 and display device 1009) in FIG. 9. The code may be stored on a computer-readable storage medium, for example, in the form of a computer program comprising a plurality of instructions executable by one or more processors. The computer-readable storage medium may be non-transitory.

At 1602, a database may be maintained by system 1600 that includes primary data. Primary data may be any data related to a user, presenter, or any other suitable entity or asset. The database may be an example common database as maintained by active unified data layer 928 in FIG. 9. In accordance with at least one embodiment, the database may include several relational databases for storing various data while maintaining relationships between the data. In accordance with at least one embodiment, associations may be maintained between pieces of data. For example, the same information may be maintained in various languages, each of which can be identified as being associated with the other language versions of the data. In accordance with at least one embodiment, supplemental information or data (data that provides an explanation for, enhances understanding of, or provides greater detail for primary data) may be associated with primary data. For example, a definition for a medical term or educational material related to the term (supplemental data) may be associated with a user chart (primary data) that contains the medical term.

At 1604, a request may be received to display a first piece of information related to the treatment of a user. In accordance with at least one embodiment, the request may be obtained from a mobile device. In these embodiments, the system 1600 may identify, based on the location of the mobile device or the location of the associated user, the display device that is closest to the user at 1606. In accordance with at least one embodiment, the request may be generated automatically (without user interaction). For example, when a presenter enters the vicinity of a display device, a request for information related to that presenter may be generated automatically. In accordance with at least one embodiment, the request may be received via input sensors located on or around the display device, such as by voice command, gesture, or keyed input.

At 1608, the system may identify at least one piece of supplemental data related to the primary information requested. Supplemental information may be queried from any number of relational databases or from the common database. In accordance with at least one embodiment, primary and/or supplemental data is filtered and/or formatted in accordance with a set of customizable rules for either the user or the presenter. This is described in greater detail elsewhere in the specification. Once the requested information and the related supplemental data is retrieved, the requested information is displayed on the display device at 1610 and the supplemental data may be provided to at least one mobile device at 1612.

In accordance with at least one embodiment of this example, a presenter may be in possession of, or associated with, a mobile device. For an example implementation of such an embodiment, the presenter may request via his mobile device that a user chart be displayed on the closest display device. The user chart may then be displayed while the mobile device is provided with more detailed user data. This allows the presenter to make a more accurate diagnosis of the user's condition without cluttering the display with details that the user may not be interested in. In accordance with at least one embodiment, the presenter may be given the ability to determine the level of detail that is displayed and/or sent to the mobile device. By way of further example, the presenter may present information to a user that prefers a language other than English. In this example, the information may be displayed in the user's preferred language on the display device and an English translation may be sent to the presenter's mobile device. As another example, a presenter may enter the vicinity of a display device. In this example, a request for information related to that presenter may be generated automatically and information related to the presenter may be displayed on the display device. When this happens, information related to the user may be sent to the presenter's mobile device.

In accordance with at least one embodiment of this example, a user may be in possession of, or associated with a mobile device. For an example implementation of such an embodiment, when treatment related information is being presented to the user, the user may be provided, via the mobile device, with educational material or definitions related to terms that appear on the display device. By way of further example, a user may prefer a language other than English. In this example, the information may be displayed in English on the display device and a translation of the information into the user's preferred language may be sent to the mobile device. In accordance with at least one embodiment, the presenter and user may each be provided with a mobile device. In this example, the same or different supplemental information may be sent to either device.

Figure 17:
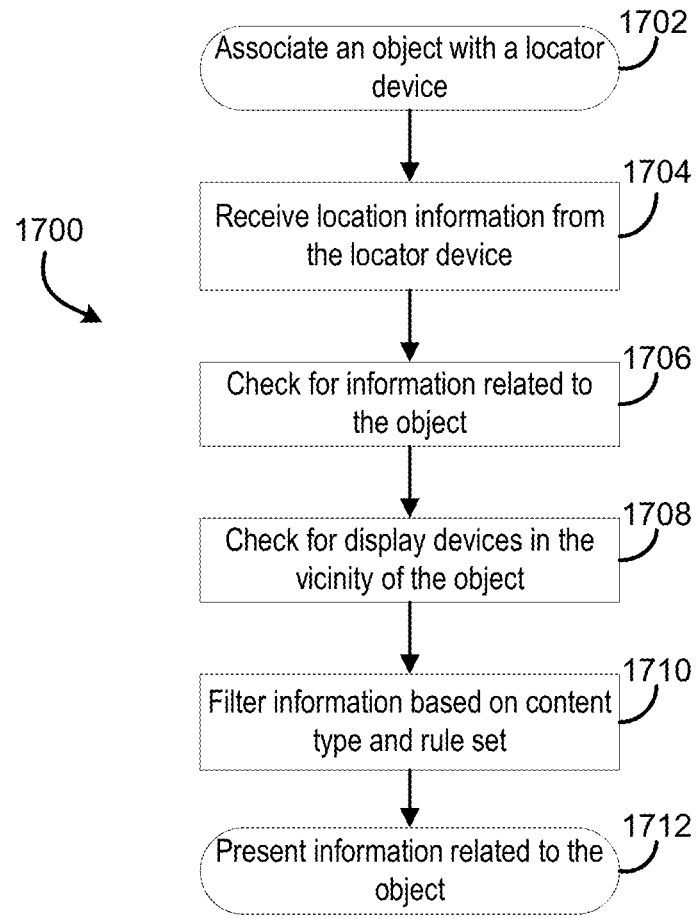
FIG. 17 illustrates an example flow diagram showing process for providing location based functionality for presentation of information to a user by a presenter, according to at least a few examples.

FIG. 17 illustrates an example flow diagram showing process 1700 for providing location based functionality for presentation of information to a user by a presenter, according to at least a few examples. Some or all of the process 1700 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof such as by the system illustrated (user devices 904, service providers 906 and display device 1009) in FIG. 9. The code may be stored on a computer-readable storage medium, for example, in the form of a computer program comprising a plurality of instructions executable by one or more processors. The computer-readable storage medium may be non-transitory.

At 1702, a database may be maintained by system 1700 that includes information relating at least one locator device to an object. For example, in a system 1700 that utilizes RTLS technology, each RTLS device may be checked out, registered to, or associated in some other way with a particular object or entity, such as a user or presenter. In another example, a mobile device that includes location tracking technology may be associated with a particular entity. The database may be maintained by the active unified data layer 928 as depicted in FIG. 9. In accordance with at least one embodiment, a locator device may be an identification device, such as a radio frequency identification (RFID) tag that is used in conjunction with RFID readers or proximity sensors placed throughout a facility.

At 1704, the system 1700 may receive location information from one of the locator devices. From the received location information, the system 1700 may determine that the locator device is in the vicinity of a display device. In accordance with at least one embodiment, the system may identify information related to the object or entity associated with the locator device at 1706. The system may also identify at least one display device in the vicinity of the object at 1708. The object-related information may be filtered and/or customized based on content or in accordance with a set of rules at 1710 and displayed on the identified display device at 1712. For example, if the display device is in a hallway, then sensitive information may be filtered out. Additionally, if the display device is located in an area with a large number of people, then a smaller segment of the display device screen may be dedicated to a particular object. Furthermore, the object or entity associated with the locator device may also be associated with a rule set for presentation of data. This is described in greater detail elsewhere in the application.

In accordance with at least one embodiment of this example, a user may be in possession of, or associated with a locator device. For an example implementation of such an embodiment, consider a scenario where a user with an RTLS locator is walking in a passageway. The system 1700 may receive location information from the RTLS device and determine the user's location. It may then be determined by the system that the user is associated with one or more user goals, one of which indicates that the user is to go to a particular department at a given time. The system may determine that the user is on his or her way to the particular department and may display, on the nearest display device, information related to the location of the department, such as an arrow or other indicator. By way of further example, a presenter may be needed in a particular department. In this example, the system may receive location information from a device associated with the presenter. The system may then, on the closest display device, display a notification directed to the presenter that he or she is needed.

Figure 18:
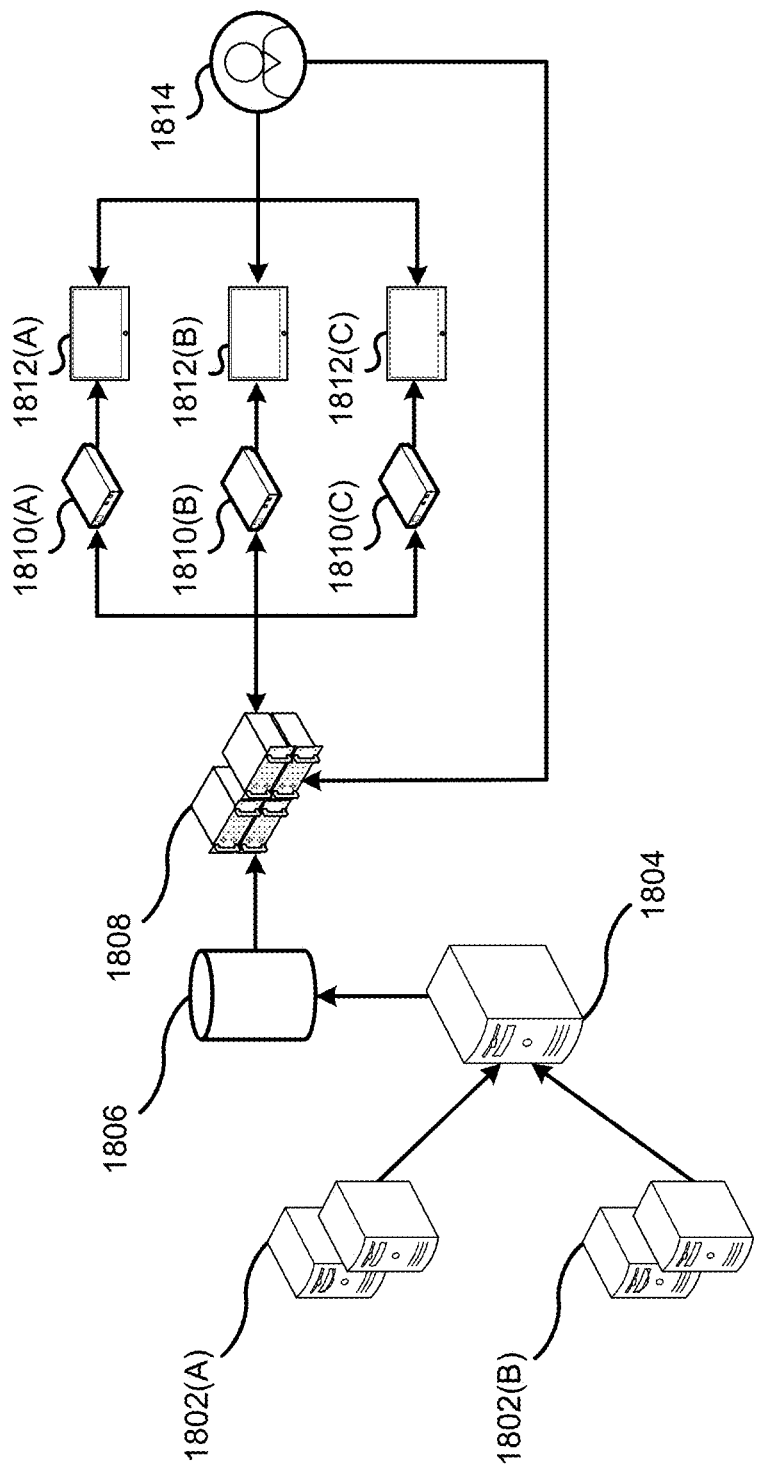
FIG. 18 illustrates a system architecture that may be implemented in accordance with at least some embodiments.

FIG. 18 illustrates a system architecture that may be implemented in accordance with at least some embodiments. In FIG. 18, a number of hardware components may be communicatively coupled and configured to implement embodiments of the disclosure. In some embodiments, multiple server clusters 1802(A) and 1802(B) may each operate and maintain user databases. In some embodiments, each of the server clusters 1802(A) and 1802(B), and respective user databases, may be independently operated by third party entities (entities unaffiliated with the operator of the described system).

Server clusters 1802 (A) and 1802 (B) may be accessible by a service provider 1804, which may be configured to compile information from the server clusters 1802 (A) and 1802 (B) into an active unified data layer 1806. In some embodiments, information from the server clusters 1802 (A) and 1802 (B) may be reformatted and/or filtered in accordance with protocols stored on the service provider 1804. For example, data may be stored in various formats across each of the server clusters 1802 (A) and 1802 (B). In this example, the service provider 1804 may be configured to retrieve information from server clusters 1802 (A) and 1802 (B), match data fields within that information to predetermined data fields, and normalize the retrieved data based on the matched data fields.

The active unified data layer 1806 may be accessed by one or more workload distributor 1808. In some embodiments, the workload distributor 1808 may be a load balancer server. The workload distributor 1808 may be configured to distribute workload requests received from multiple thin client devices 1810 (A-C) across multiple server devices for processing. Additionally, the workload distributor 1808 may be configured to retrieve information on behalf of one or more thin client devices 1810 and/or process retrieved information on behalf of one or more thin client devices 1810. In some embodiments, the workload distributor 1808 may be configured to provide information to a thin client device 1810 in a manner that it is to be presented via a display device 1812.

The multiple thin client devices 1810 (A-C) may each be in communication with one of a plurality of display devices 1812 (A-C). In some embodiments, an "electronic whiteboard" may comprise a thin client device coupled with a display device. In at least some of these embodiments, the thin client device and display device may comprise a single device.

A real-time location services (RTLS) system 1814 may also be in communication with the thin client devices 1810 (A-C) and/or the workload distributor 1808. Each individual person (presenters and users) as well as system resources (medical devices, equipment, etc.) may be tracked via the RTLS system 1814. In some embodiments, the RTLS system 1814 may be configured to provide updated location data on a periodic basis (e.g., every second, every ten seconds, every minute, etc.).

In accordance with at least some embodiments, the RTLS system 1814 may provide an list of all people as well as system resources in the vicinity of a display device 1812 to the display device 1812 and/or the workload distributor 1808. The system may identify the display device 1812 relevant to the list and determine the types of information that should be displayed via that display device. In some embodiments, the type of information to be displayed may depend on a category of at least one presenter on the provided list or people/resources. In some embodiments, the presence of a piece of equipment may prompt the system to retrieve information on that piece of equipment to be presented on the display device 1812.

Upon receiving a list of people/resources within the vicinity of a display device 1812, the list may be arranged in an order of priority. A set of configuration settings (e.g., rules and/or preferences) may be retrieved for each of the people/resources on the list. In some embodiments, the system may, for each person/resource on the list in their specified priority order, select configuration settings that do not conflict with already selected configuration settings. In this way, a set of configuration settings may be generated that best fit the list of people/resources according to priority. Information derived from the active unified data layer 1806 may then be customized according to the generated set of configuration settings.

For example, in some embodiments, the system may dictate that a user's preferences take priority over a presenter's preferences. In this example, the system may determine that a user is in a room with a presenter that includes a display device 1812 and may assign a higher priority to the user than to the presenter. In this example, if a user only speaks Spanish, but does not require any specific arrangement/format of information, and the presenter speaks English and does require a specific arrangement/format of information, then a set of configuration settings may be generated that includes Spanish as the language and the specific arrangement/format of information required by the presenter. In some embodiments, an English version of the information may be provided to a separate mobile device in the possession of the presenter.

FIG. 19 illustrates an example of a graphical user interface display that may be implemented on an electronic display device in accordance with at least some embodiments. In FIG. 19, a number of user-specific data points may be presented via a graphical user interface (GUI) executed on an electronic whiteboard in accordance with a generated set of configuration settings. As described above, an electronic whiteboard may comprise a computing device (either a thick client device or a thin client device) communicatively coupled to a display device.

In accordance with at least some embodiments, an RTLS system may provide location information to a service provider which includes location information associated with a number of people and/or resources. In some embodiments, each of the people and/or resources may be in possession of a locator device (e.g., a locator bracelet). The service provider may be configured to manage content provided to a plurality of remotely located electronic whiteboards. Upon receiving location information from the RTLS system, the service provider may determine, for each of the plurality of electronic whiteboards, a user within the vicinity of the electronic whiteboard. The service provider may determine, from configuration settings stored in relation to the user, a number of user-specific details to be presented to the user. Additionally, the service provider may identify a number of additional users who are authorized to access user-specific information. For example, the service provider may identify an attending care team currently assigned to the user. In some embodiments, the service provider may cause the electronic whiteboard to display information related to users 1904 assigned to the user.

In some embodiments, the service provider may identify a number of users within a vicinity of an electronic whiteboard. The service provider may retrieve information related to each of those users (e.g., name, title/role, availability, etc.) from a database. In some embodiments, the service provider may retrieve an image associated with that user. For example, the service provider may access a Human Resources (HR) application to retrieve an image stored in association with the user. The information related to the identified users may subsequently be provided to an electronic whiteboard to be presented. For example, the electronic whiteboard may present information, including an image, on users assigned to the user in its vicinity so that the user may easily ascertain each user's role. Additionally, as a new user is detected within the vicinity of the electronic whiteboard, the service provider may identify the user, retrieve information related to that user, and cause a notification 1906 to be presented on the electronic whiteboard. In some embodiments, the service provider may re-compile a set of configuration settings to be used in filtering/formatting information presented on the electronic whiteboard to include configuration settings for that user.

As depicted in FIG. 19, a GUI 1902 executed on an electronic whiteboard may be caused to display a number of user-specific details. In some embodiments, the type of details and/or format of presentation may be dictated by one or more configuration setting relevant to the user or another present user. For example, the service provider may cause the electronic whiteboard to display a set of user goals 1908 for a particular user that is within the vicinity of the electronic display device. Additionally, the electronic whiteboard may be caused to display one or more configuration settings 1910 that are to be used to filter/format information.

In accordance with at least some embodiments, the service provider may be configured to identify information relevant to a user based on configuration settings. The service provider may cause this information to be displayed on the electronic whiteboard. For example, if a procedure associated with the user is scheduled to occur, the service provider may retrieve instructions associated with the procedure to be provided to the user. By way of illustration, if a user is scheduled to undergo a procedure, and the service provider determines that the procedure requires the user to fast for 12 hours prior to the procedure, then the service provider may cause the electronic whiteboard to display instructions to the user to fast. In some embodiments, the instructions may be provided when they become relevant. In some embodiments, the service provider may identify educational materials or other information relevant to various configuration settings to be provided to the user. For example, upon determining that a user is on a heart healthy diet, the service provider may make a recommendation of heart healthy foods, or of foods to avoid. In some embodiments, information presented to the user in GUI 1902 may be filtered according to various configuration settings. For example, if the user is on a heart-healthy diet, then the service provider may display only those menu items that fall within the category of heart-healthy when viewing a menu.

Figure 20:
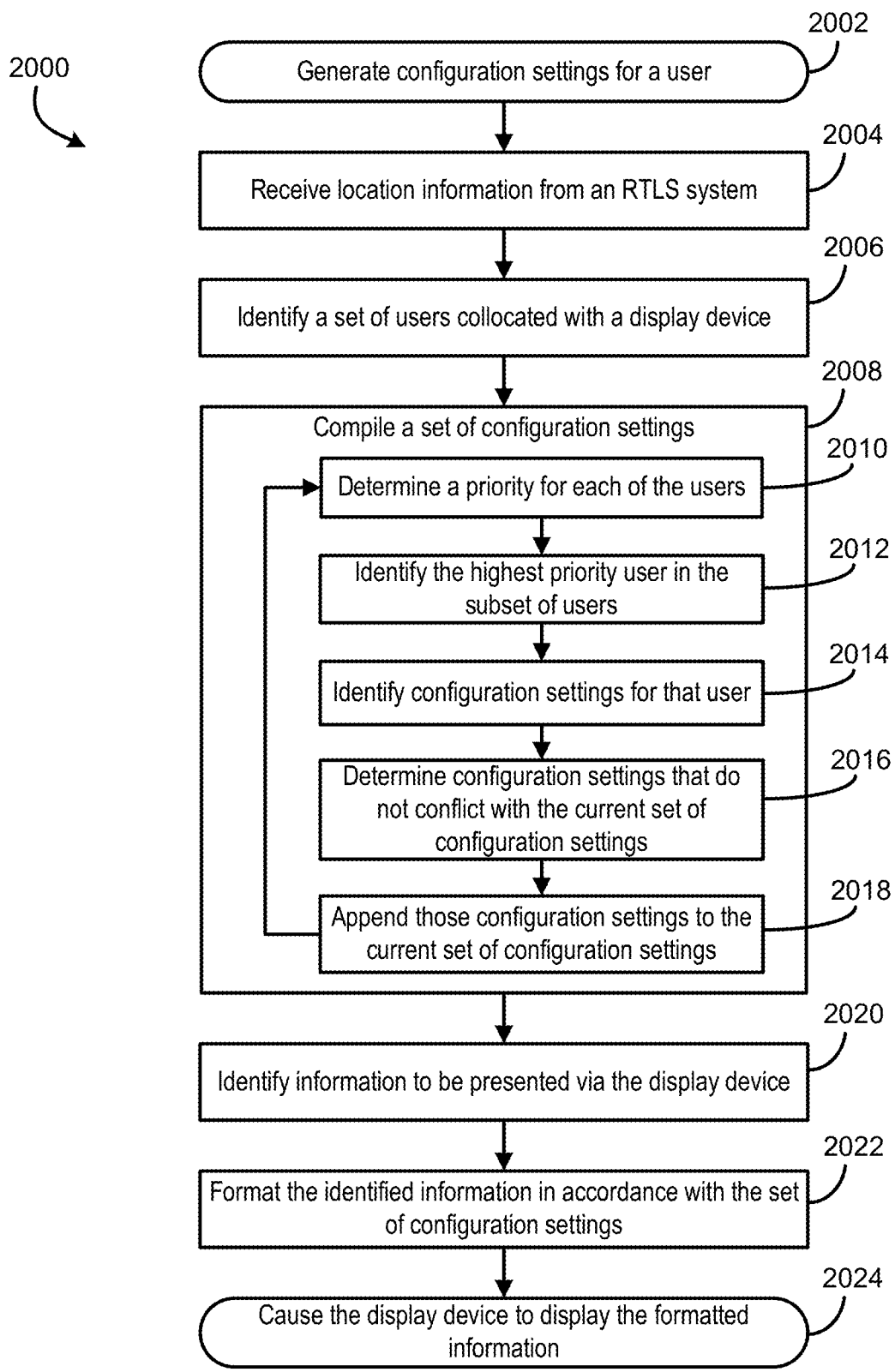
FIG. 20 illustrates an example flow diagram showing process 2000 for generating a set of configuration settings and applying those configuration settings to displayed information in accordance with at least some embodiments.

FIG. 20 illustrates an example flow diagram showing process 2000 for generating a set of configuration settings and applying those configuration settings to displayed information in accordance with at least some embodiments. In accordance with at least some embodiments, process 2000 may be performed by a service provider computer, such as an example service provider computer 906 displayed in FIG. 9.

Process 2000 may begin at 2002, when a service provider receives configuration settings relevant to a user. In some embodiments, the configuration settings may be gathered during an enrollment phase. For example, upon admitting a user to a hospital for the first time, the user may be asked a series of questions (e.g., language preferences, etc.) that may be translated by the service provider into configuration settings. Additionally, a user may add and/or alter configuration settings for that user or another user. For example, a presenter may alter a dietary restriction configuration setting for a user based on his or her diagnosis of that user. In some embodiments, default configuration settings may be applied to each user of the system unless they are otherwise altered. For example, each user may be defaulted to have English as a preferred language unless that user specifies another language.

At 2004, the service provider may receive location information from an RTLS system. For example, each user involved with the system may be in possession of a real-time locator tag (e.g., an RTLS bracelet). The RTLS system may, on a periodic or continuous basis, provide location information to the service provider for each currently active RTLS tag. In some embodiments, a display device or other system hardware components may also include locator tags, and the RTLS system may provide location information related to those system components to the service provider.

At 2006, the service provider may identify a set of users within a vicinity of an electronic whiteboard device. For example, the service provider may identify each user within a predetermined distance of a display device. In some embodiments, the service provider may maintain a repository of display device locations. Upon receiving location information from the RTLS system, the service provider may determine that one or more users is within, has entered, or is about to enter, the vicinity of a particular display device.

The service provider may generate a set of configuration settings to apply to information presented on the display device. To do this, the service provider may perform a subprocess 2008. In some embodiments, the service provider may initiate subprocess 2008 upon determining that an information request has been received with respect to a particular user and/or display device once the service provider has determined the set of users in the vicinity of the requestor. In some embodiments, subprocess 2008 may be initiated each time that a user enters and/or exits the vicinity of the display device to determine which configuration settings are most appropriate for the set of collocated users (users located within the same vicinity).

Subprocess 2008 may begin at 2010, when a priority is determined for each of the users in the set of users. In at least some embodiments, a presentee (e.g., an intended audience of information to be presented) may be indicated. For example, the service provider may receive an indication of a presentee in a received information request. In another example, a presentee status may be defaulted to a user within the set of collocated users. In some embodiments, presenters may be assigned a priority based on their rank and/or role within the system. It should be noted that there are a number of other ways in which a priority may be assigned to users in a set of collocated users that would be apparent to one skilled in the art.

At 2012, the service provider may identify the user within the set of collocated users having the highest priority. In some embodiments, the presentee may be assigned a highest priority. In some embodiments, users may be ranked in priority according to role, title, and/or position. In some embodiments, the users may be manually ranked (e.g., via the information request). In some embodiments, particular types of information requests may be assigned a particular way in which priority should be determined for a set of collocated users.

At 2014, the service provider may identify configuration settings associated with the highest priority user. For example, upon determining which user in the setoff users is associated with the highest priority, the service provider may retrieve configuration settings associated with that user. At 2016, the service provider may compare each of the retrieved configuration settings associated with the highest priority user with the configuration settings in the current set of configuration settings to determine if the configuration setting creates a conflict. For example, if the set of configuration settings already includes a configuration setting appended with respect to another user that is incompatible with the current configuration setting being processed, then the current configuration setting may be determined to be in conflict with the set of configuration settings.

At 2018, the service provider may append each of the non-conflicting configuration settings to the current set of configuration settings. Subprocess 2008 may be repeated for each of the users in the set of users in order of assigned priority. For example, subprocess 2008 may first be performed with respect to the highest priority user, and subsequently with respect to the second highest priority user, and then each of the remaining users in order of priority. In this way, the set of configuration settings may be compiled that is optimized for a particular set of users.

At 2020, process 2000 may continue when the service provider identifies information to be presented via the electronic whiteboard. For example, the service provider may receive a request to present information via an electronic whiteboard. In some embodiments, the service provider may receive a general information request from a user and may identify the types of information to be provided based on a role and/or title of that user. For example, if a radiologist submits a request to view information related to a user, then the service provider may, by default, identify information related to x-ray scans. Additionally, the service provider may automatically determine the user related to the request based on that user being a member of the set of collocated users. In some embodiments, a user may submit a request for information from a mobile device in communication with the service provider.

It should be noted that step 2020 may be performed prior to 2006. For example, a user may submit a request to have information displayed on a display device within his or her vicinity (e.g., via a mobile device in the possession of that user). In this example, upon receiving a request from the user for specific information, the service provider may determine other users within that user's vicinity as well as a display device. In this example, the set of configuration settings may be generated according to subprocess 2008 upon determining a set of users to which the information is being presented.

At 2022, the identified information may be formatted in accordance with the set of configuration settings. For example, the service provider may identify information requirements associated with each of the configuration settings in the set of configuration settings. In this way, the information to be presented may be optimally formatted and/or filtered based on the requirements of a set of users to be presented the information.

At 2024, the formatted information may be provided to the electronic whiteboard device and caused to be displayed. In some embodiments, the information presented may be controlled via customized information display commands (e.g., custom gestures as depicted in FIG. 11) associated with a presenter. In some embodiments, a copy of the information may be formatted in accordance with a second set of configuration settings and may be provided to a second display device. For example, a presenter may submit a request to present information to a user on a local electronic whiteboard via his or her mobile device. Upon receiving the request for information related to the user, the service provider may initiate process 2000 to cause the requested information to be displayed on the electronic whiteboard. In addition, the service provider may format the information in accordance with the submitting presenter's configuration settings and may subsequently provide that formatted information to the mobile device from which the information is received. In this way, multiple versions of the information may be provided, each of which is optimally customized for a particular audience.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction (s) and/or data.

While the principles of the disclosure have been described above in connection with specific apparatuses and methods, it is to be clearly understood that this description is made only by way of example and not as limitation on the scope of the disclosure.

What is claimed is:

1. A system, comprising:
   a display device associated with a display device location;
   a real-time location system configured to report location information associated with a plurality of users;
   a plurality of locator devices in communication with the real-time location system, wherein each of the plurality of users are in possession of a locator device of the plurality of locator devices;
   a system management device in communication with the plurality of locator devices and in communication with the real-time location system, the system management device comprising:
   a processor device; and
   a memory including instructions that, when executed with the processor device, cause the system to, at least:
   maintain configuration settings in association with the plurality of users, the configuration settings comprising an indication of a role associated with each user of the plurality of users;
   receive location information associated with one or more collocated users of the plurality of users within a vicinity of the display device location, the one or more collocated users including a target user and at least one other user;

determine, based on the configuration settings maintained in association with the one or more collocated users, one or more roles associated with the at least one other user;

identify target user-specific information that characterizes a medical condition of the target user of the one or more collocated users, wherein a type of information included in the target user-specific information is identified based on a medical specialty of a first user of the at least one other user, and the target user-specific information includes test results that characterize the medical condition of the target user and are related to the medical specialty of the first user;

cause the target user-specific information to be presented to the one or more collocated users on the display device; and provide additional target user-specific information that characterizes the medical condition of the target user to a mobile device that is associated with the first user, wherein the additional target user-specific information includes more details than the target user-specific information, and the additional target user-specific information is related to the medical specialty of the first user.

2. The system of claim 1, wherein each role associated with each user of the plurality of users is assigned a priority, and wherein the instructions further cause the system to identify a highest-priority role from the one or more roles associated with the at least one other user.

3. The system of claim 2, wherein the type of information included in the target user-specific information is identified based on the highest-priority role from the one or more roles associated with the at least one other user.

4. The system of claim 1, wherein information related to the one or more collocated users is also presented on the display device.

5. The system of claim 4, wherein the information related to the one or more collocated users comprises at least an image of each of the one or more collocated users.

6. The system of claim 1, wherein identifying the target user-specific information comprises identifying information to be prevented from being presented on the display device based on at least one role of the one or more roles associated with the one or more collocated users.

7. The system of claim 1, further comprising a plurality of mobile devices communicatively coupled to the system management device, wherein the plurality of mobile devices includes the mobile device that is associated with the first user.

8. The system of claim 7, wherein the target user-specific information relevant to the target user of the one or more collocated users is identified in response to receiving an information request from the mobile device that is associated with the first user.

9. A computer-implemented method comprising:

maintaining configuration settings in relation to a plurality of users, the configuration settings comprising an indication of a role associated with each user of the plurality of users;

receiving location information related to a subset of the plurality of users, the subset of the plurality of users including a target user and at least one other user, the location information including an indication of coordinates of each user in the subset of the plurality of users;

identifying, based on the received location information and based on location information maintained with respect to a plurality of display devices, a display device of the plurality of display devices within a vicinity of the subset of the plurality of users;

determining a role for each of the at least one other user based on the configuration settings maintained with respect to each of the users in the subset of the plurality of users;

retrieving, with respect to the target user of the subset of the plurality of users, a set of target user information that characterizes a medical condition of the target user, wherein a type of information included in the set of target user information is retrieved based on a medical specialty of a first user of the at least one other user, and the set of target user information includes test results that characterize the medical condition of the target user and are related to the medical specialty of the first user;

causing the set of target user information to be displayed on the identified display device; and providing additional target user information that characterizes the medical condition of the target user to a mobile device that is associated with the first user, wherein the additional target user information includes more details than the set of target user information, and the additional target user information is related to the medical specialty of the first user.

10. The computer-implemented method of claim 9, wherein the set of target user information is retrieved automatically.

11. The computer-implemented method of claim 9, further comprising determining a priority for each user of the at least one other user based on the determined role for that user.

12. The computer-implemented method of claim 11, wherein the set of target user information is formatted according to formatting information associated with the user of the at least one other user having a highest priority.

13. The computer-implemented method of claim 9, wherein the set of target user information is retrieved in response to receiving an information request from the mobile device that is associated with the first user.

14. An electronic whiteboard device comprising:

a display device;

a processor device; and a memory including instructions that, when executed with the processor device, cause the electronic whiteboard device to, at least:

receive a first request for information to be presented on the display device of the electronic whiteboard device;

receive an indication of a set of users proximate to the electronic whiteboard device, the set of users including a target user and at least one other user;

identify each of the users in the set of users;

identify configuration settings associated with each of the users in the set of users;

identify roles for each of the at least one other user in the set of users based on the configuration settings;

generate a second request for information that characterizes a medical condition of the target user, the second request for information including an indication of the identified roles;

send the second request for information to a service provider, such that a type of the information retrieved by the service provider is determined based on a medical specialty of a first user of the at least one other user, and the information includes test results that characterize the medical condition of the target user and are related to the medical specialty of the first user;

receive, from the service provider and in response to the second request for information, the information that characterizes the medical condition of the target user;

display the received information via the display device; and provide additional information that characterizes the medical condition of the target user to a mobile device that is associated with the first user, wherein the additional information includes more details than the received information, and the additional information is related to the medical specialty of the first user.

15. The electronic whiteboard device of claim 14, wherein identifying the configuration settings associated with each of the users in the set of users comprises:

providing an indication of the set of users to the service provider; and receiving, from the service provider, the configuration settings associated with each of the users in the set of users.

16. The electronic whiteboard device of claim 14, wherein at least a portion of the received information is filtered out in accordance with at least one role associated with a user of the at least one other user.

17. The electronic whiteboard device of claim 16, wherein the portion of the received information is sensitive information that is prevented from being displayed on the electronic whiteboard device.

18. The electronic whiteboard device of claim 14, wherein the first request for information to be presented on the display device of the electronic whiteboard device is received from a mobile device in communication with the electronic whiteboard device.

19. The electronic whiteboard device of claim 14, wherein the first request for information to be presented on the display device of the electronic whiteboard device includes an indication of a presentee.

* * * * *